(12) United States Patent
Trussardi

(10) Patent No.: US 10,590,156 B2
(45) Date of Patent: Mar. 17, 2020

(54) GALNAC CLUSTER PHOSPHORAMIDITE

(71) Applicant: Hoffmann-La Roche Inc., Little Falls, NJ (US)

(72) Inventor: Rene Trussardi, Basel (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 15/978,815

(22) Filed: May 14, 2018

(65) Prior Publication Data

US 2018/0258122 A1 Sep. 13, 2018

Related U.S. Application Data

(63) Continuation of application No. PCT/EP2016/077516, filed on Nov. 14, 2016.

(30) Foreign Application Priority Data

Nov. 16, 2015 (EP) .................................... 15194811

(51) Int. Cl.
*C07H 15/08* (2006.01)
*C07H 21/04* (2006.01)
*C07H 1/00* (2006.01)

(52) U.S. Cl.
CPC .............. *C07H 15/08* (2013.01); *C07H 1/00* (2013.01); *C07H 21/04* (2013.01); *Y02P 20/55* (2015.11)

(58) Field of Classification Search
None
See application file for complete search history.

(56) References Cited

U.S. PATENT DOCUMENTS

2011/0207799 A1 8/2011 Rozema et al.

FOREIGN PATENT DOCUMENTS

| WO | 2010/108125 | 9/2010 |
|----|---|---|
| WO | 2011/104169 | 9/2011 |
| WO | 2012/083046 | 6/2012 |
| WO | 2012/083046 A2 | 6/2012 |
| WO | 2012/083185 | 6/2012 |
| WO | 2014/179620 A1 | 6/2014 |
| WO | 2014/207232 | 12/2014 |
| WO | 2015/071388 | 5/2015 |
| WO | 2015/168589 | 11/2015 |

OTHER PUBLICATIONS

ISR of PCT/EP2016/077516 (Date of mailing Jan. 30, 2017).
Thazha P. Prakash et al., "Solid-phase synthesis of 5'-triantennary N-acetylgalactosamine conjugated antisense oligonucleotides using phosphoramidite chemistry" Bioorganic & Medicinal Chemistry Letters 25(19):4127-4130 (Aug. 8, 2015).
CAS Registry entry for Registry No. 1185198-47-3, Sep. 16, 2009.
CAS Registry entry for Registry No. 133170-57-7, Apr. 12, 1991.
CAS Registry entry for Registry No. 156917-23-9, Aug. 10, 1994.
Chakravarty et al., "Plasmin-Activated Prodrugs for Cancer Chemotherapy. 2. Synthesis and Biological Activity of Peptidyl Derivatives of Doxorubicin" Journal of Medicinal Chemistry 26(5):638-644 (Jan. 1, 1983).
Iselin et al., "Derivate von L-Methionin-sulfoxyd and ihre Verwendung für Peptidsynthesen" Helvetica Chimica ACTA 44(1):61-78 (Oct. 24, 1961).

(Continued)

*Primary Examiner* — Layla D Berry
(74) *Attorney, Agent, or Firm* — Todd M. Crissey

(57) ABSTRACT

The invention comprises GalNAc phosphoramidite derivatives of the formula I

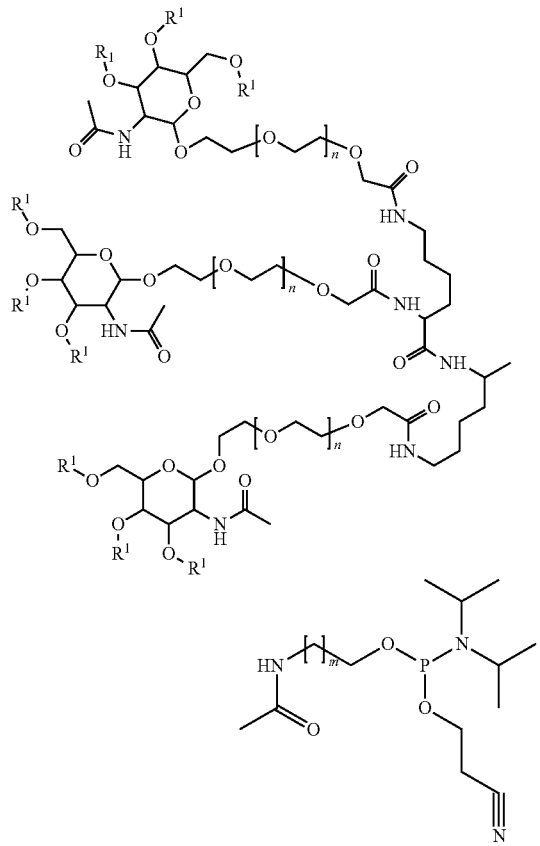

wherein $R^1$ is a hydroxy protecting group, n is an integer from 0 to 10 and m is an integer from 0 to 20 and its corresponding enantiomers and/or optical isomers thereof. The invention further comprises a process for the preparation of the GalNAc phosphoramidite derivatives of the formula I and its use in the preparation of therapeutically valuable GalNAc-cluster oligonucleotide conjugates.

19 Claims, No Drawings
Specification includes a Sequence Listing.

(56) References Cited

OTHER PUBLICATIONS

ISR and Written Opinion of PCT/EP2016/068361 (dated Sep. 19, 2016).
Kessler and Iselin, "Selektive Spaltung substituierter Phenylsulfenyl-Schutzgruppen bei Peptidsynthesen" Helvetica Chimica ACTA 49(4):1330-1344 (Jan. 1, 1966).
MacMillan et al., "Evaluation of alternative solvents in common amide coupling reactions: replacement of dichloromethane and N,N-dimethylformamide" Green Chemistry 15:596-600 ( 2013).
Maruzen et al., "Synthesis of Organic Compounds IV-Carboxylic Acid" The Chemical Society of Japan 5th Edition:121-123 ( 2005).
Nitecki et al., "The Synthesis of the Pentapeptide Related to the gm(a) Antigen of human gamma G-Globulin" Australian Journal of Chemistry 22(4):871-874 (Jan. 1, 1969).
Schiesser et al., "Synthesis and DNA-Damaging Properties of Cisplatin-N-Mustard Conjugates" European Journal of Organic Chemistry 2015(12):2654-2660 (Apr. 13, 2015).
Zhao et al., "N-(2-Chloro-9H-purin-6-yl)-N-cyclopropylglycylamino acids and derivatives Synthesis,evaluation as a class of novel analgesics, and 3D QSAR analysis" Bioorganic & Medicinal Chemistry 17:6305-6310 (Sep. 1, 2009).

GALNAC CLUSTER PHOSPHORAMIDITE

CROSS REFERENCE TO RELATED APPLICATIONS

This application is a continuation of International Application No. PCT/EP206/077516 having an international filing date of Nov. 14, 2016, the entire contents of which are incorporated herein by reference, and which claims benefit under 35 U.S.C. § 119 European Patent Application No. 15194811.4 filed Nov. 16, 2015.

SEQUENCE LISTING

The instant application contains a Sequence Listing submitted via EFS-Web and hereby incorporated by reference in its entirety. Said ASCII copy, created on May 10, 2018 is named P33193US_SeqList.txt, and is 1,280 bytes in size.

FIELD

Provided herein are compounds, processes for making compounds, and methods of using compounds described herein as building blocks in the solid phase oligonucleotide synthesis.

SUMMARY

Provided herein, inter alia, are GalNAc phosphoramidite compounds and salts thereof comprising formula I:

wherein $R^1$ is a hydroxy protecting group, n is an integer from 0 to 10 and m is an integer from 0 to 20, corresponding enantiomers and/or optical isomers thereof.

In another aspect provided herein are processes for the preparation of a GalNAc phosphoramidite derivative of the formula I. Such processes comprise (a) reacting a GalNAc acid derivative of formula III described herein with an amine of formula IV described herein to form an amide of formula V described herein; (b) removing the hydroxy protecting group to form the GalNAc acid amide of formula VI described herein; and (c) reacting the GalNAc acid amide of formula VI with a phosphoroamidating agent to form the GalNAc phosphoramidite derivative of the formula I.

In another aspect provided herein are methods and uses of the GalNAc phosphoramidite compounds having formula I for the preparation of GalNAc-cluster oligonucleotide conjugates.

The present embodiments may be understood more fully by reference to the detailed description and examples, which are intended to exemplify non-limiting embodiments.

DETAILED DESCRIPTION

The following definitions are set forth to illustrate and define the meaning and scope of the various terms used to describe the invention herein.

Whenever a chiral carbon is present in a chemical structure, it is intended that all stereoisomers associated with that chiral carbon are encompassed by the structure as pure stereoisomers as well as mixtures thereof.

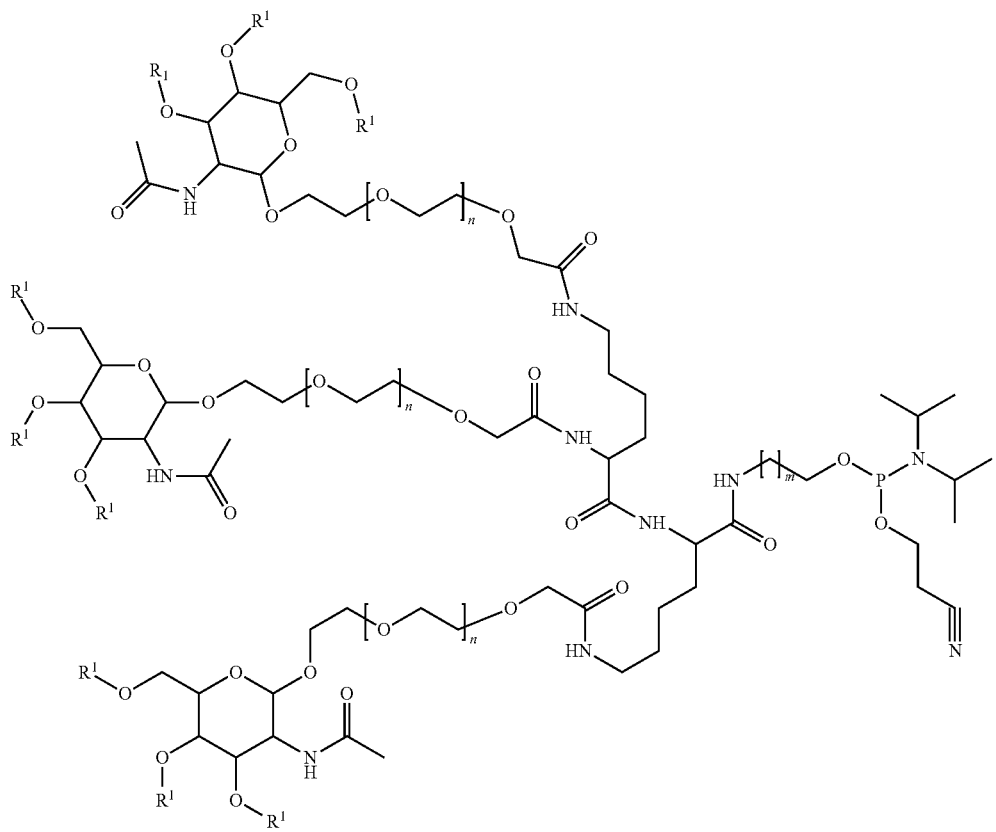

(I)

The term "$C_{1-12}$-alkyl" denotes a monovalent linear or branched saturated hydrocarbon group of 1 to 12 carbon atoms, and in more particular embodiments 1 to 6 carbon atoms. Examples of alkyl include methyl, ethyl, propyl, isopropyl, n-butyl, iso-butyl, sec-butyl, tert-butyl, and pentyl and hexyl with its isomers.

The term "acyl" denotes a carbonyl group which is linked to an alkyl group. The term particularly stands for a $C_{1-12}$-alkylcarbonyl group, more particularly a $C_{1-6}$-alkylcarbonyl group which is optionally substituted by $C_{1-6}$-alkyl or optionally substituted by phenyl. Examples for acyl groups are acetyl, pivaloyl or benzoyl. Optional substitutions for phenyl are halogen such as chlorine, bromine or iodine or a $C_{1-6}$-alkyl group as defined above.

The term "hydroxy-protecting group" denote groups which are intended to protect a hydroxy group and include ester- and ether-forming groups, in particular tetrahydropyranyl, acyl (e.g. benzoyl, acetyl, carbamoyl), benzyl and silylethers (e.g. TBS, TBDPS) groups. Further examples of these groups are found in T. W. Greene and P. G. M. Wuts, "Protective Groups in Organic Synthesis", 2nd ed., John Wiley & Sons, Inc., New York, N.Y., 1991, chapters 2-3; E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981.

The term "halogen" stands for fluorine, chlorine, bromine or iodine.

Compounds:

GalNAc phosphoramidites of formula I carry the GalNAc moiety which is the targeting moiety of conjugates comprising the GalNAc moiety. The GalNAc moiety, due to its affinity to the asialoglycoprotein receptor which is located on the liver cell enables functional delivery of oligonucleotide conjugates to the liver cell. Such GalNAc cluster conjugates have the potential to act as pharmacokinetic modulators and therefore be therapeutically valuable compounds as e.g. described in the PCT Publication WO 2012/083046 or in the US Patent Application Publication US 2011/0207799.

Due to the unique combination of the GalNAc moiety and phosphoramidite, the GalNAc phosphoramidites of formula I as described herein can directly be introduced as building blocks together with the nucleoside building blocks in the solid phase oligonucleotide synthesis. A separate conjugation step to introduce the GalNAc moiety can therefore be avoided.

In a preferred embodiment the GalNAc phosphoramidite derivatives described herein have the formula I:

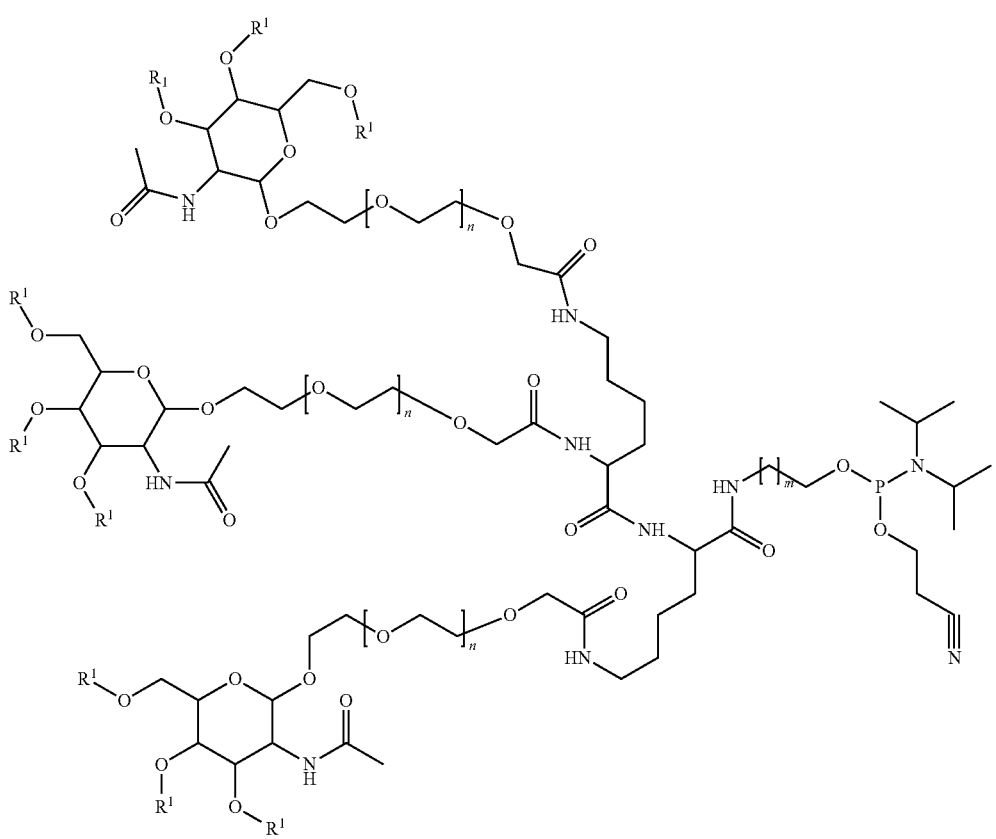

(I)

wherein $R^1$ is a hydroxy protecting group as described herein;
n is an integer from 0 to 10; and
m is an integer from 0 to 20;
or an enantiomer or optical isomer thereof.

In one embodiment, the hydroxy protecting group $R^1$ is an acyl group. In another embodiment, $R^1$ is $C_{1-12}$-alkylcarbonyl group, more particularly a $C_{1-6}$-alkylcarbonyl group which is optionally substituted by $C_{1-6}$-alkyl or phenyl. The preferred hydroxy protecting group $R^1$ can be selected from acetyl, pivaloyl or benzoyl, whereby acetyl is the most preferred.

n is preferably an integer from 0 to 5, more preferably from 1 to 3, but most preferred is 2. m is preferably an integer from 0 to 10, more preferably from 3 to 7, but most preferred is 5.

In a preferred embodiment the GalNAc phosphoramidite derivatives have the formula Ia:

(Ia)

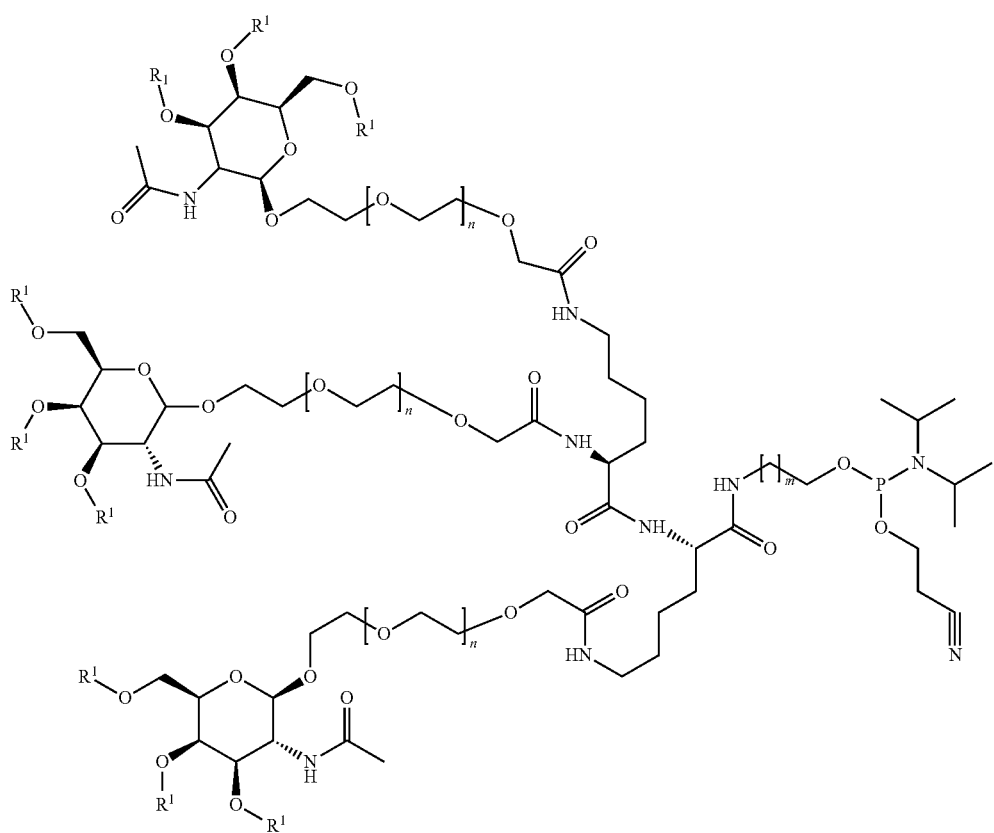

wherein n and m are as defined herein.

Preferably $R^1$ of the GalNAc phosphoramidite derivative described herein is acyl; n is 0, 1, 2, 3, 4, or 5 and m is 0, 1, 2, 3, 4, 5, 6, 7, 8, 9 or 10, more preferably $R^1$ of the GalNAc phosphoramidite derivative or an enantiomer or optical isomer thereof of formula Ia is acetyl, pivaloyl or benzoyl; n is 1, 2 or 3 and m is 3, 4, 5, 6, or 7.

In an even more preferred embodiment the GalNAc phosphoramidite derivative has the formula Ib:

(Ib)

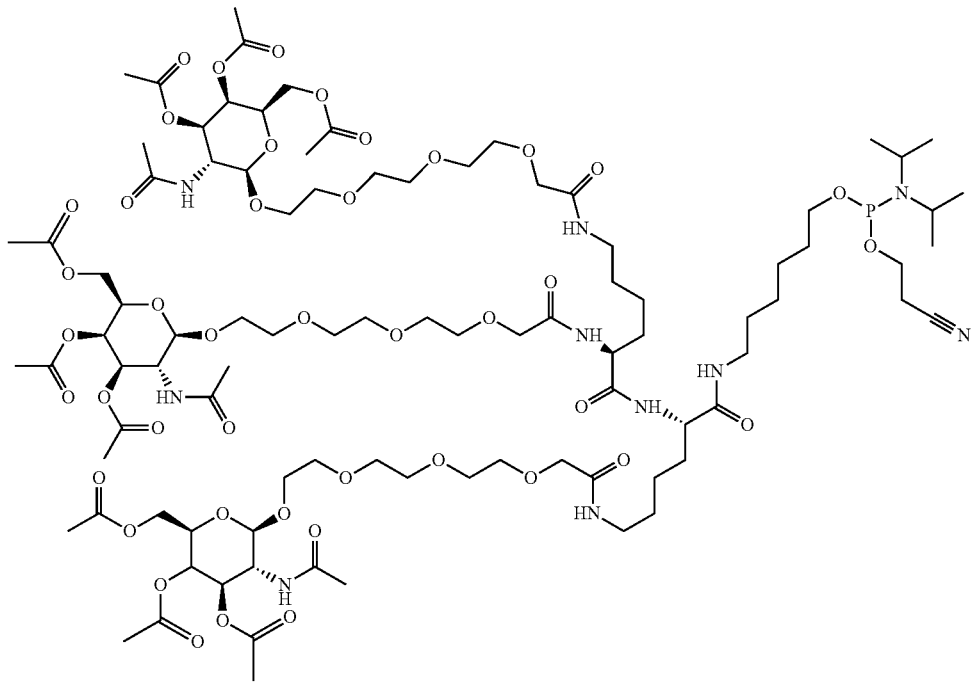

which corresponds to formula Ia with $R^1$=acetyl, n=2 and m=5.

Further provided herein are processes for the preparation of a GalNAc phosphoramidite derivative of the formula I. In one aspect is a process, comprising:

a) reacting a GalNAc acid derivative of formula III

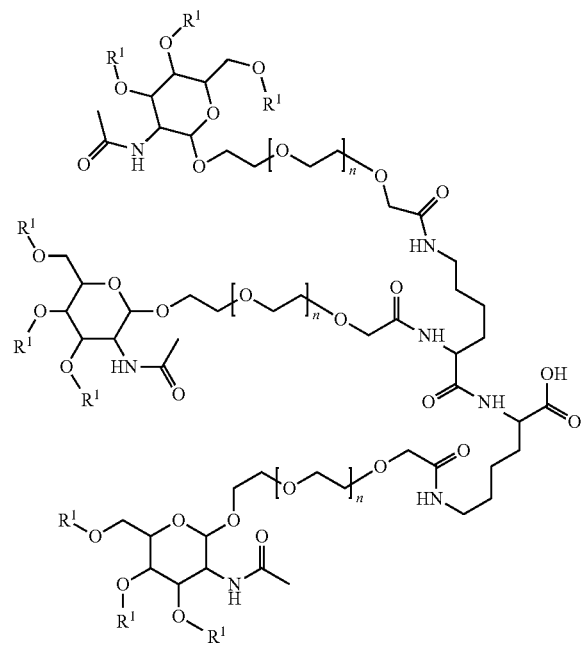

(III)

where $R^1$ and n are as defined herein;
with an amine of formula IV:

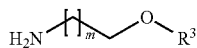

(IV)

wherein $R^3$ is a hydroxy protecting group as described herein and m is as described herein, thereby forming an amide of formula V:

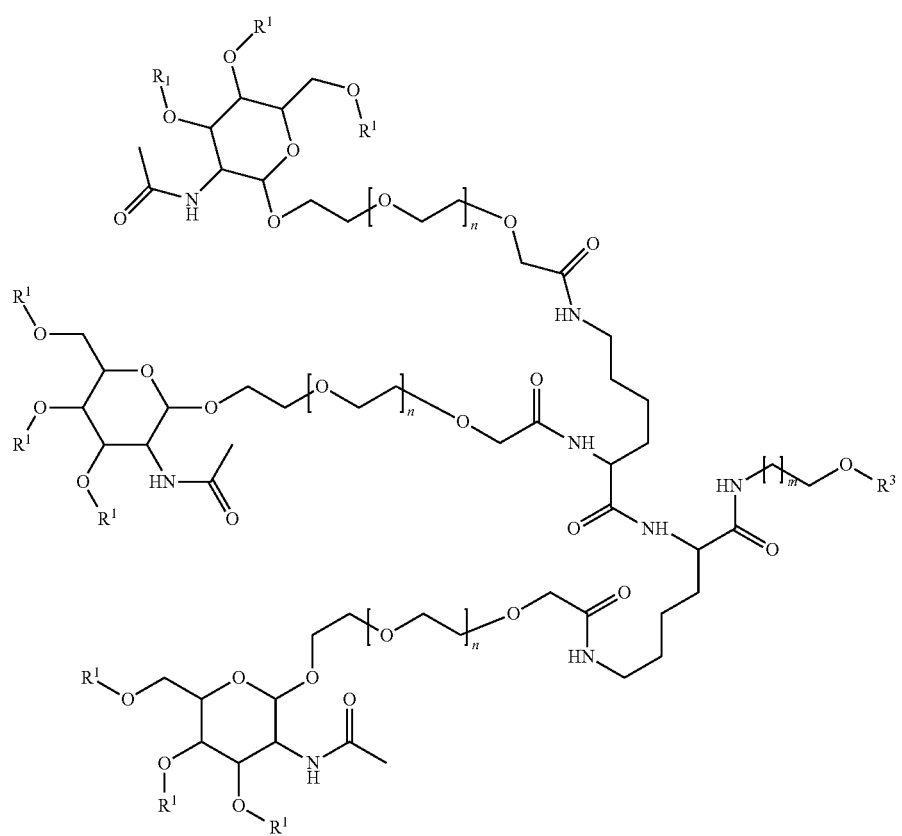

(V)

wherein $R^1$, $R^3$, n and m are as defined herein;

b) removing $R^3$ to form the GalNAc acid amide of formula VI:

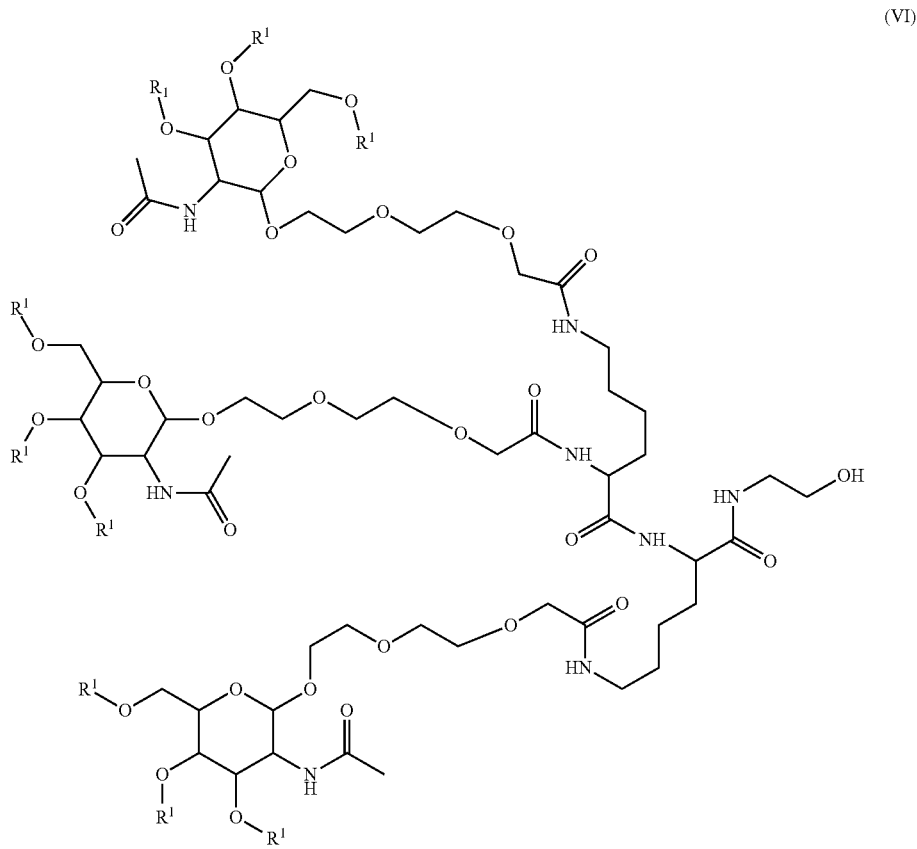

(VI)

wherein n, and m are as defined herein; and c) reacting the GalNAc acid amide of formula VI with a phosphoroamidating agent to form the GalNAc phosphoramidite derivative of the formula I.

Step a) of the processes described herein comprises the reaction of a GalNAc acid derivative of formula III with the amine of formula V. The benzylester precursor of the Gal-NAc derivative of formula III can be prepared according to the Scheme 1 below. Subsequent hydrogenolysis of the benzylester by way of a catalytic hydrogenation with hydrogen in the presence of a hydrogenation catalyst such as for instance with palladium on charcoal delivers the GalNAc derivative of formula III.

Scheme 1:

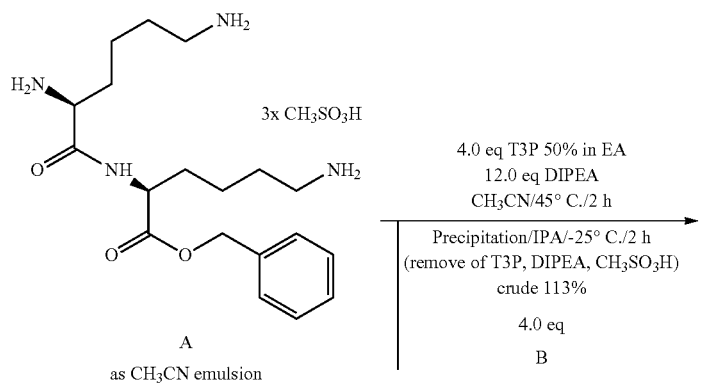

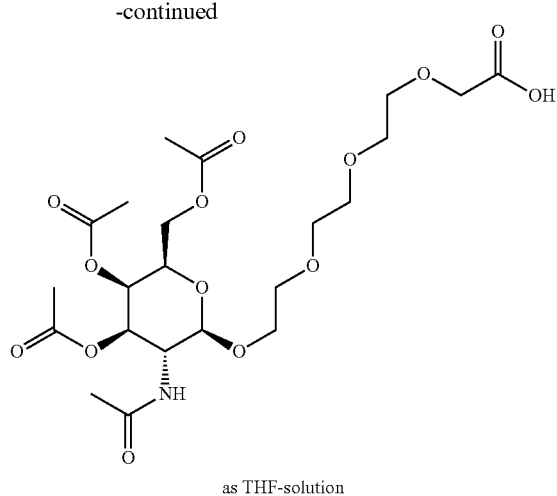

as THF-solution

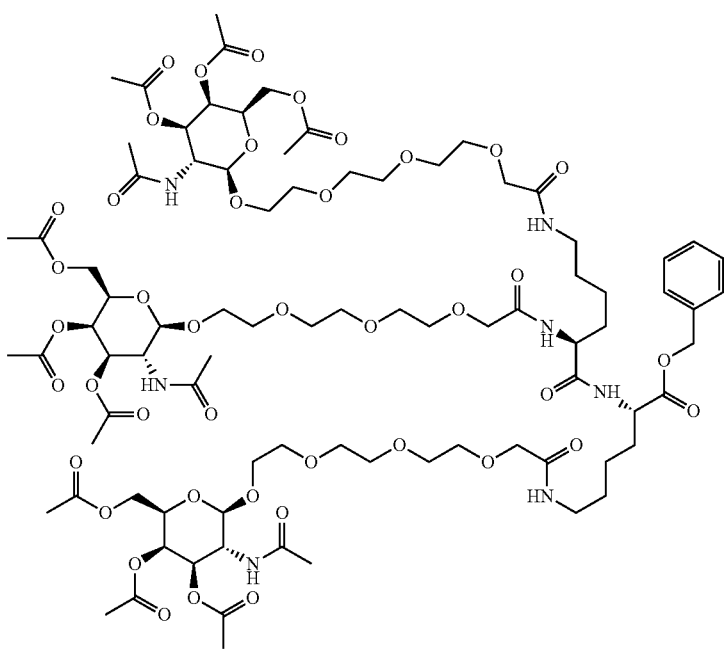

The amine of formula V can be prepared as exemplified herein for the 6-benzyloxyhexan-1-amine in the Scheme 2 below. The reaction is for instance substantially the same as described in Saneyoshi, Hisao et al, *Organic Letters,* 16(1), 30-33; 2014 or in Alvarez, M. et al, *Anales de Quimica, Serie C: Quimica Organica y Bioquimica,* 83(2), 155-61; 1987 or Alvarez, M. et al, *Journal of Medicinal Chemistry,* 30(7), 1186-93; 1987. Starting from a commercially available halogenhexanoxymethylbenzene the respective isoindoline-1,3-dione is formed with a 1,3 dioxoisoindolin salt. Suitable 1,3 dioxoisoindolin salts are the alkali salts like the sodium- or potassium salt or the tetraalkylammonium salts such as the tetrabutylammonium-salt. In a subsequent step the isoindoline-1,3-dione group can be cleaved with hydrazine or with a primary amine, preferably methylamine to form the free amine.

Scheme 2:

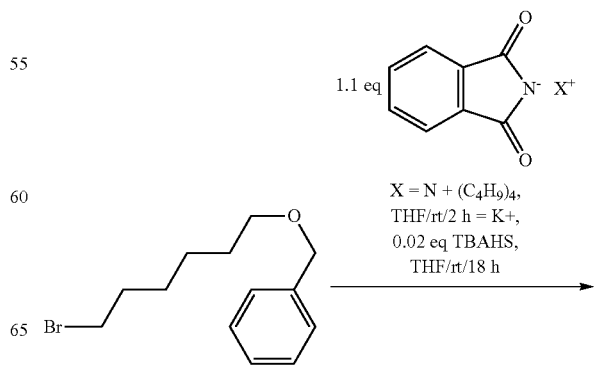

-continued

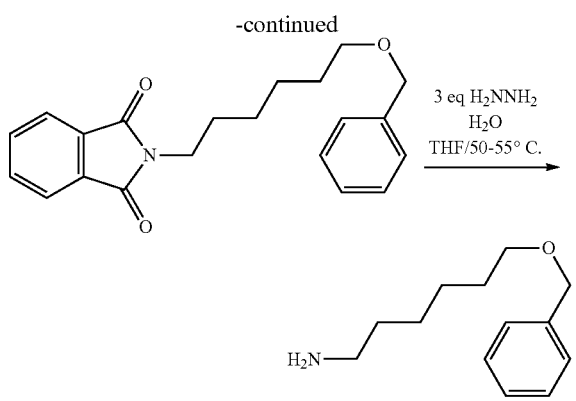

The amide formation in step a) is performed in the presence of a peptide coupling agent, an amine base and an organic solvent.

The coupling can follow the classical methods known to the skilled in the art using a carbodiimide coupling agent like DCC (N,N'-Dicyclohexylcarbodiimide) and an additive like HOBt (1-hydroxybenztriazole), HOSu (N-hydroxysuccinimide), TBTU (N,N,N',N'-Tetramethyl-O-(benzotriazol-1-yl)uronium tetrafluoroborate, HBTU (2-(1H-benzotriazol-1-yl)-1,1,3,3-tetramethyluronium hexafluorophosphate) or HOAt (1-Hydroxy-7-azabenzotriazole and common combination thereof such as TBTU/HOBt or HBTU/HOAt.

In a preferred embodiment, n-propylphosphonic acid anhydride (T3P) is selected as coupling agent together with a tertiary amine base, like for example, triethylamine or N-ethyldiisopropylamine, but preferably with N-ethyldiisopropylamine.

The coupling reaction usually takes place in a polar aprotic solvent like acetonitrile or tetrahydrofuran or mixtures thereof at reaction temperatures in the range of 20° C. and 70° C., preferably in the range of 20° C. and 40° C.

The crude amide of formula V product can be isolated by evaporation of the solvent. Further purification of the product can be achieved, when needed, by preparative reversed phase chromatography using an apolar stationary phase and a polar mobile phase such as acetonitrile/water or by SFC (supercritical fluid chromatography) using $CO_2$/methanol/ethanol/2-propanol.

Step b) requires the removal of the hydroxy protecting group $R^3$ to form the GalNAc acid amide of formula VI. It is important that the hydroxy protecting group $R^3$ is chemically different from the hydroxy protecting group $R^1$, such that removal conditions can be selected in a manner that the hydroxy protecting group $R^3$ is cleaved while the hydroxy protecting group $R^1$ remains unaffected. A suitable hydroxy protecting group $R^3$ is benzyl which is optionally substituted by halogen or $C_{1-6}$-alkyl or $R^3$ is benzhydryl or trityl, i.e. a group which can be cleaved by hydrogenolysis. Alternatively $R^3$ is silyl like tert. butyl dimethyl silyl. Silyl groups can be cleaved in the presence of fluoride ions A suitable hydroxy protecting group $R^3$ is benzyl which is optionally substituted by halogen or $C_{1-6}$-alkyl or $R^3$ is benzhydryl or trityl, i.e. a group which can be cleaved by hydrogenolysis. Alternatively $R^3$ is silyl like tert. butyl dimethyl silyl. Silyl groups can be cleaved in the presence of fluoride ions.

In a preferred embodiment $R^3$ is benzyl and the hydrogenolysis is a catalytic hydrogenation with hydrogen in the presence of a suitable hydrogenation catalyst. Suitable hydrogenation catalyst for the removal of the benzyl group is palladium on carbon (Pd/C). The reaction is usually performed in the presence of polar aprotic solvent like acetonitrile or tetrahydrofuran or mixtures thereof at reaction temperatures between 0° C. and 40° C., preferably 10° C. and 30° C. and at a hydrogen pressure of 1 bar to 5 bar.

The GalNAc acid amide of formula VI can be separated by filtering off the catalyst and removing the solvent by evaporation.

Step c) requires the reaction of the GalNAc acid amide of formula VI with a phosphoroamidating agent as described herein to form the GalNAc phosphoramidite derivative of the formula I.

The phosphoroamidating agent can be selected from 2-cyanoethyl-N,N-di-(2-propyl)chlorophosphoroamidite or from 2-Cyanomethyl-N,N,N',N'-tetra(2-propyl) phosphorodiamidite.

Where 2-Cyanomethyl-N,N,N',N'-tetra(2-propyl)phosphorodiamidite is used, the reaction is performed in the presence of an activating compound like tetrazole, 5-(ethylthio)-1H-tetrazole, 5-(benzylthio)-1H-tetrazole or 4,5-di cyanoimidazole.

In a preferred embodiment 2-cyanoethyl-N,N-di-(2-propyl) chlorophosphoroamidite is chosen. The reaction is then performed in the presence of a tertiary amine such as triethylamine and a polar aprotic solvent like acetonitrile or tetrahydrofuran or mixtures thereof at a reaction temperature between −20° C. and 50° C., preferably in acetonitrile at a reaction temperature between 0° C. and 20° C.

The GalNAc phosphoramidite derivative of the formula I can as a rule be separated from the triethylamine hydrochloride by filtration. The filtrate with the crude product can be used directly for the solid phase nucleotide synthesis without further purification.

Further provided herein are methods of preparing a therapeutically valuable GalNAc-cluster oligonucleotide conjugate from the GalNAc phosphoramidite derivatives described herein. Such methods comprise:

a2) preparing a GalNAc phosphoramidite derivative of formula I as described herein;

b2) contacting the synthesized GalNAc phosphoramidite derivative of formula I of step a2 using oligonucleotide solid phase synthesis with a nucleoside building block and repeating the contacting steps with another nucleoside building block to form a GalNAc-cluster oligonucleotide conjugate bound to the solid support; and c2) cleaving and deprotecting the GalNAc-cluster oligonucleotide conjugate of step b2 from the solid phase support, thereby forming a therapeutically valuable GalNAc-cluster oligonucleotide conjugate.

In one embodiment, the GalNAc phosphoramidite derivative or enantiomer thereof comprises formula Ia. In one embodiment, the GalNAc phosphoramidite derivative or enantiomer thereof comprises formula Ib.

The term oligonucleotide as used herein is defined as it is generally understood by the skilled person as a molecule comprising two or more covalently linked nucleosides. For use as a therapeutically valuable oligonucleotide, oligonucleotides are typically synthesized as 7-30 nucleotides in length. Oligonucleotides are commonly made in the laboratory by solid-phase chemical synthesis followed by purification. When referring to a sequence of the oligonucleotide, reference is made to the sequence or order of nucleobase moieties, or modifications thereof, of the covalently linked nucleotides or nucleosides. Oligonucleotides described herein are man-made, chemically synthesized, and purified or isolated. Oligonucleotides described herein can comprise one or more modified nucleosides or nucleotides as understood in the art. In some embodiments, the oligonucleotide is an antisense oligonucleotide.

The oligonucleotides may consist of DNA, RNA, modified RNA or LNA nucleoside monomers or combinations thereof. The LNA nucleoside monomers are modified nucleosides which comprise a linker group (referred to as a biradicle or a bridge) between C2' and C4' of the ribose sugar ring of a nucleotide. These nucleosides are also termed bridged nucleic acid or bicyclic nucleic acid (BNA) in the literature.

In a non-limiting embodiment, the oligonucleotide may be selected from the group consisting of:

```
                                                  (COMP NO 10)
5'-caG_SᵐC_SG_St_Sa_Sa_Sa_Sg_Sa_Sg_Sa_SG_SG-3';

(COMP NO 11)
5'-caG_SᵐC_SG_St_Sa_Sa_Sa_Sg_Sa_Sg_Sa_SG_SG_ST-3';

(COMP NO 12)
5'-caG_SᵐC_SG_St_Sa_Sa_Sa_Sg_Sa_Sg_SA_SG_SG-3';

(COMP NO 13)
5'-caG_SG_SᵐC_SG_St_Sa_Sa_Sa_Sg_Sa_Sg_Sa_SG_SG-3';

(COMP NO 14)
5'-caA_SG_SᵐC_Sg_Sa_Sa_Sg_St_Sg_Sc_Sa_Sc_SA_SᵐC_SG-3';

(COMP NO 15)
5'-caA_SG_SᵐC_Sg_Sa_Sa_Sg_St_Sg_Sc_Sa_Sc_Sa_SC_SG_SG-3';

(COMP NO 16)
5'-⁽⁵⁻ᴮʳ⁾caG_SᵐC_SG_St_Sa_Sa_Sa_Sg_Sa_Sg_Sa_SG_SG-3';

(SEQ ID NO 1),
5'-cagcgtaaagagagg-3';
and (COMP NO 18),
5'-A_SA_ST_Sg_Sc_St_Sa_Sc_Sa_Sa_Sa_Sa_Sc_SC_SC_SA-3';
``` wherein uppercase letters denote beta-D-oxy-LNA units; lowercase letters denote DNA units; the subscript "s" denotes a phosphorothioate linkage; superscript m denotes a DNA or beta-D-oxy-LNA unit containing a 5-methylcytosine base, superscript 5-Br denotes a DNA unit containing a 5-bromocytosine base.

Using the GalNAc phosphoramidite derivative of the formula I as building block in the oligonucleotide solid phase synthesis allows introducing the GalNAc moiety together with a suitable amino linker at the 5'end of the oligonucleotide and to form desired GalNAc-cluster oligonucleotide conjugates. In a non-limiting embodiment, the GalNAc-cluster oligonucleotide conjugates may be selected from the group consisting of:

```
                                                   (COMP NO 1)
GalNAc-cluster-AM-C6-5'-caG_SᵐC_SG_St_Sa_Sa_Sa_Sg_Sa_Sg_Sa_SG_S

G-3';

(COMP NO 2)
GalNAc-cluster-AM-C6-5'-caG_SᵐC_SG_St_Sa_Sa_Sa_Sg_Sa_Sg_Sa_SG_S

G_ST-3';

(COMP NO 3)
GalNAc-cluster-AM-C6-5'-caG_SᵐC_SG_St_Sa_Sa_Sa_Sg_Sa_Sg_SA_SG_S

G-3';

(COMP NO 4)
GalNAc-cluster-AM-C6-5'-caG_SG_SᵐC_SG_St_Sa_Sa_Sa_Sg_Sa_Sg_Sa_S

G_SG-3';

(COMP NO 5)
GalNAc-cluster-AM-C6-5'-caA_SG_SᵐC_Sg_Sa_Sa_Sg_St_Sg_Sc_Sa_Sc_S

A_SᵐC_SG-3';

(COMP NO 6)
GalNAc-cluster-AM-C6-5'-caA_SG_SᵐC_Sg_Sa_Sa_Sg_St_Sg_Sc_Sa_Sc_S a_Sc_SG_SG-3';

(COMP NO 7)
GalNAc-cluster-AM-C6-5'-⁽⁵⁻ᴮʳ⁾caG_SᵐC_SG_St_Sa_Sa_Sa_Sg_Sa_Sg_S a_SG_SG-3';

(COMP NO 8)
GalNAc-cluster-AM-C6-5'-cagcgtaaagagagg-3';

(COMP NO 9)
GalNAc-cluster-AM-C6_S-5'-A_SA_ST_Sg_Sc_St_Sa_Sc_Sa_Sa_Sa_Sa_Sc_S

C_SC_SA-3';
``` wherein AM-C6 denotes a 6-aminohexyl-1-phosphate or a 1-thiophosphate linkage of the formula:

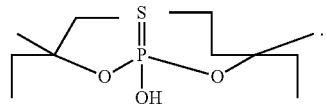 [SMILES: CCCC(C)(CC)OP(O)(=S)OC(C)(CC)CC]

After solid phase synthesis the GalNAc-cluster oligonucleotide conjugate remains bound on the solid support and carries protection groups like the hydroxy protecting group $R^1$ as well as protecting groups attached to the oligonucleotides used during synthesis. Cleavage from the support and deprotection can happen using methods known to the skilled in the art and described in the literature such as in Wincott et al.; *Nucl. Acids Res.* (1995) 23 (14): 2677-2684. Usually the GalNAc-cluster oligonucleotide conjugate is obtained in the form of a suitable salt such the ammonium salt or the alkali metal salt like the sodium or potassium salt.

The compounds disclosed herein have a nucleobase sequence selected from the group consisting of SEQ ID NO 1, 2, 4 and 5:

```
SEQ ID NO: 1:
cagcgtaaag agagg (Comp 1, 3, 4, 7, 8, 10, 12 13,
16 & 17);

SEQ ID NO: 2:
cagcgtaaag agaggt (Comp 2 & 11);

SEQ ID NO: 3:
caagcgaagt gcacacg (Comp 5 & 14);

SEQ ID NO: 4:
caagcgaagt gcacacgg (Comp 6 & 15);
and

SEQ ID NO: 5:
aatgctacaa aaccca (Comp 9 & 18),
```

EXAMPLES

Abbreviations

AcOH acetic acid
DMAP 4-(dimethylamino)-pyridine
DMF N, N'-dimethylformamide
EtOH ethanol
MeOH methanol
rt room temperature (20-25° C.)
THF tetrahydrofuran
MTBE methyl tert.-butyl ether Synthesis of the GalNAcAcid Precursor. Building Block A:

Example 1

Benzyl (2S)-6-(tert-butoxycarbonylamino)-2-(9H-fluoren-9-ylmethoxycarbonylamino) hexanoate

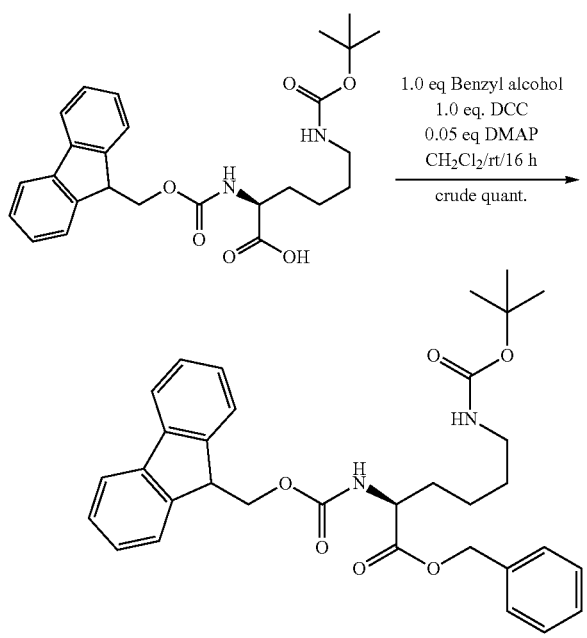

234.0 g (500.0 mmol) (2S)-6-(tert-butoxycarbonylamino)-2-(9H-fluoren-9-ylmethoxycarbonylamino)hexanoic acid was suspended in 500 ml dichloromethane, 62.0 ml (600 mmol, 1.2 eq) benzyl alcohol and 3.05 g DMAP (25.0 mmol, 0.05 eq) were added. The solution was cooled to 0-5° C. in the course of 40 min, a solution of 108.0 g (525.0 mmol, 1.05 eq) N,N'-dicyclohexyl carbodiimide in 500 ml dichloromethane, was added dropwise. The white suspension was stirred for 1 h at 0-5° C. and then for 15 h at room temperature. The suspension was filtered over a G3 glass filter, the white filter cake was washed portion-wise with total 250 ml dichloromethane. The filtrate was evaporated at 650-10 mbar/1 h to obtain a yellow oil, which was in dissolved in 2.0 L ethyl acetate, extracted with 2.0 L 0.5M hydrochloric acid, 2.0 L 1M NaHCO$_3$ and 1.0 L brine, the organic layer was evaporated to dryness at 40° C./150-10 mbar/5 h to obtain 291.1 g crude benzyl (2S)-6-(tert-butoxycarbonylamino)-2-(9H-fluoren-9-ylmethoxycarbonylamino) hexanoate as white solid in 104% yield and 96.4% purity (HPLC area-%; contains ca. 5% benzyl alcohol). The material was used in the next step without further purification. MS: m/z=459.22735 (M-boc+H)$^+$.

Example 2

Benzyl (2S)-2-amino-6-(tert-butoxycarbonylamino)hexanoate methanesulfonic Acid Salt

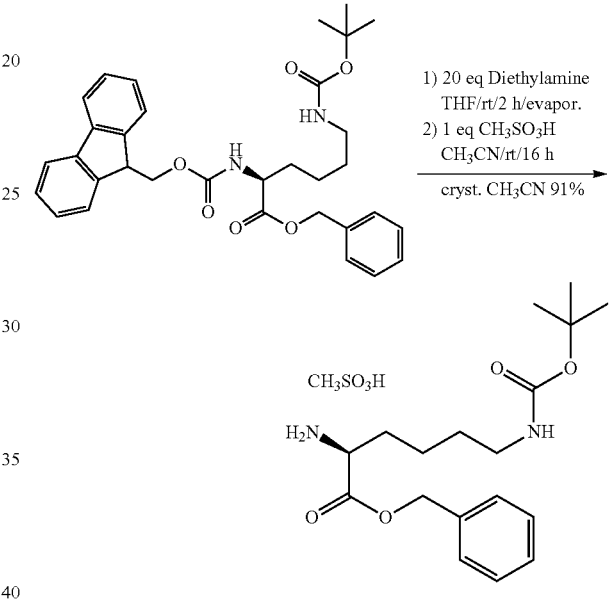

291.1 g Benzyl (500.0 mmol) (2S)-6-(tert-butoxycarbonylamino)-2-(9H-fluoren-9-ylmethoxycarbonylamino) hexanoate (HPLC purity; 95.8%; contains ca. 5% benzyl alcohol) were dissolved in 1.4 L THF at room temperature. Within 10 min, 1.04 L diethylamine (10.0 mol, 20 eq) were added, the light yellow solution was stirred for 2 h at room temperature and then evaporated at 40° C./200-10 mbar, 200 ml acetonitrile was added and evaporated again to efficiently remove diethylamine at 40° C./100-10 mbar/1 h. Finally, 268.1 g of a yellow oil was obtained, which was dissolved in 2.5 L acetonitrile, stirred for 10 min at room temperature. Insoluble particles were filtered over a glass fiber filter and washed with 500 ml acetonitrile. The filtrate was treated dropwise in the course of 10 min with 34.0 ml methanesulfonic acid at 20° C.-25° C. The formed white suspension was stirred for 17 h at room temperature and filtered over a G3 glass filter. The filter cake was washed portion-wise with 500 ml acetonitrile. The white crystals were dried at 40° C./15 mbar/4 h to obtain 195.8 g benzyl (2S)-2-amino-6-(tert-butoxycarbonylamino)hexanoate methanesulfonic acid salt as white crystals in 91% yield (2 steps) and 99.3% purity (HPLC area-%). MS: m/z=337.2149 (M+H)$^+$.

Example 3

Benzyl (2S)-2-[[(2S)-2,6-bis(tert-butoxycarbonylamino)hexanoyl]amino]-6-(tert-butoxycarbonylamino)hexanoate

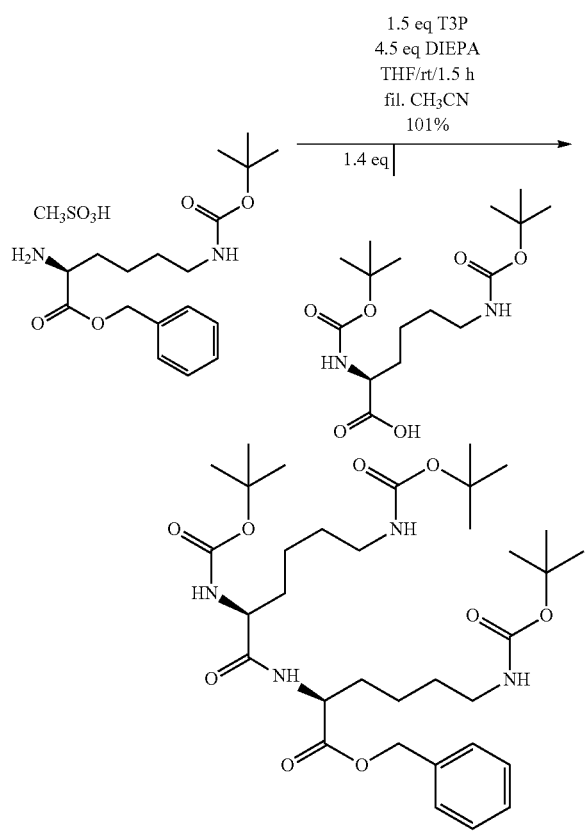

190.0 g (439.0 mmol) Benzyl (2S)-2-amino-6-(tert-butoxycarbonylamino) hexanoate methanesulfonic acid salt were suspended in 1.9 L THF at room temperature. 335 ml (1.98 mol, 4.5 eq) N-ethyldiisopropylamine were added whereby the temperature slightly decreased to 15° C. Next, 213 g (615 mmol, 1.4 eq) (S)-2,6-bis((tert-butoxycarbonyl)amino) hexanoic acid were added and the white suspension was stirred at room temperature for 20 min. 390 ml n-propylphosphonic acid anhydride (T3P as cyclic trimer 50% in ethyl acetate, 659 mmol, 1.5 eq) were added dropwise in the course of 20 min at 20-25° C. (cooled in a cool water bath). The resulting light yellow, cloudy solution was stirred at room temperature for 1.5 h, transferred to a separating funnel, diluted with 1.9 L MTBE and extracted with 1.9 L water, 1.9 L 0.5M hydrochloric acid, 1.9 L0.5M NaOH, 1.9 L water and 1.9 L brine. The separated, still cloudy organic layer was filtered over a glass fiber filter, the filter was washed with 100 ml MTBE and the combined filtrates were evaporated at 40° C./100 mbar/1 h, 1.0 L MTBE (to aceotropic remove water) were added again and evaporated at 40° C./250-10 mbar/1 h to obtain crude 296.4 g as white solid residue.

The crude solid was treated with 500 ml acetonitrile and the cloudy solution was heated to 60-65° C. for 10 min. The mixture was cooled to 20-25° C., stirred for 10 min, filtered over a glass fiber filter and washed with 50 ml acetonitrile. The light yellow solution was evaporated at 40° C./100-10 mbar/4 h to obtain 295 g benzyl (2S)-2-[[(2S)-2,6-bis(tert-butoxycarbonylamino)hexanoyl]amino]-6-(tert-butoxycarbonylamino)hexanoate as off-white solid in a yield of 101% (HPLC purity: 100%, diastereomer purity (SS) 98.6%) which was used without further purification in the next step. MS: m/z=565.3741 (M-boc+H)$^+$.

Example 4

Benzyl (2S)-6-amino-2-[[(2S)-2,6-diaminohexanoyl]amino]hexanoate tri-methanesulfonic Acid Salt

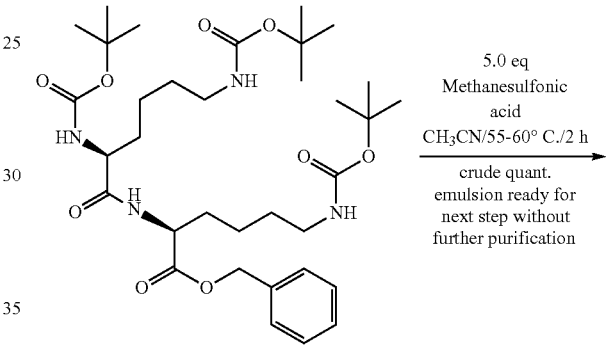

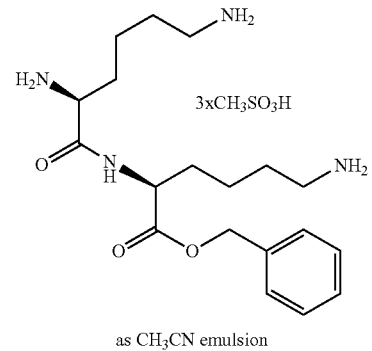

124.0 g (187 mmol) benzyl (2S)-2-[[(2S)-2,6-bis(tert-butoxycarbonylamino) hexanoyl]amino]-6-(tert-butoxycarbonylamino)hexanoate was suspended in 1.25 L acetonitrile. 61.0 ml (935.0 mmol, 5.0 eq) methanesulfonic acid was added at 20-25° C. in the course of 10 min (gas evolution). The resulting orange suspension was heated in 40 min to 55-60° C. and stirred for another 1 h at 55-60° C. The orange-red emulsion was cooled to room temperature (debocation was controlled by $^1$H-NMR) and used without further purification in the A+B assembly step, example 8. MS: m/z=365.2558 (M+H)$^+$.

Building Block B:

Example 5a

Benzyl 2-[2-[2-(2-hydroxyethoxy)ethoxy]ethoxy]acetate

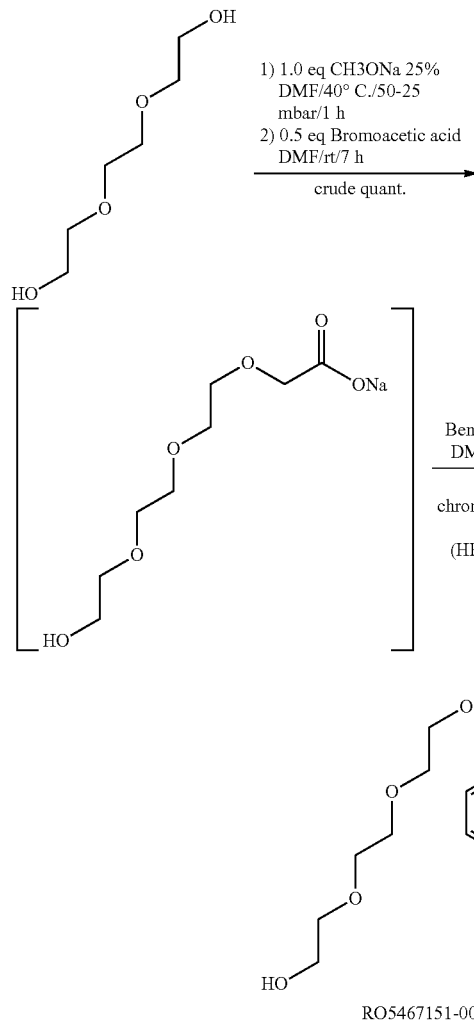

RO5467151-000

30.0 g (200.0 mmol), 2-[2-(2-Hydroxyethoxy)ethoxy]ethanol were dissolved in 50 ml DMF, at 20-25° C., then, 46.0 ml sodium methoxide 25% (200.0 mmol, 1.0 eq) in methanol were added. The formed solution was evaporated at 40° C./50 mbar/0.5 h (remove of 40 ml solvent), 50 ml DMF was added again and evaporated at 40° C./20 mbar/0.5 h (remove of 15 ml solvent), To the slightly jellylike suspension a solution of 13.9 g bromoacetic acid (100 mmol, 0.5 eq) in 50 ml DMF was added at 20-25° C. and the mixture was stirred for 6 h. 11.9 ml benzyl bromide (100 mmol, 0.5 eq) was added and the mixture stirred for another 16 h at 20-25° C. The reaction mixture was then treated with 200 ml brine and extracted with 200 ml MTBE. The separated MTBE layer was extracted with 200 ml brine, the separated MTBE layer was then dried with anhydrous sodium sulfate, filtered and evaporated at 40° C./300-10 mbar/1 h to obtain crude 23.9 g benzyl 2-[2-[2-(2-hydroxyethoxy)ethoxy]ethoxy]acetate.

After chromatography (600 g silica 60 (0.063-0.2 mm), mobile phase: ethyl acetate) a total of 7.85 g benzyl 2-[2-[2-(2-hydroxyethoxy)ethoxy]ethoxy]acetate as colorless oil was isolated in 13% yield and 99.0% purity (HPLC area-%). MS: m/z=299.1517 (M+H)$^+$.

Example 5b

Benzyl 2-[2-[2-(2-hydroxyethoxy)ethoxy]ethoxy]acetate

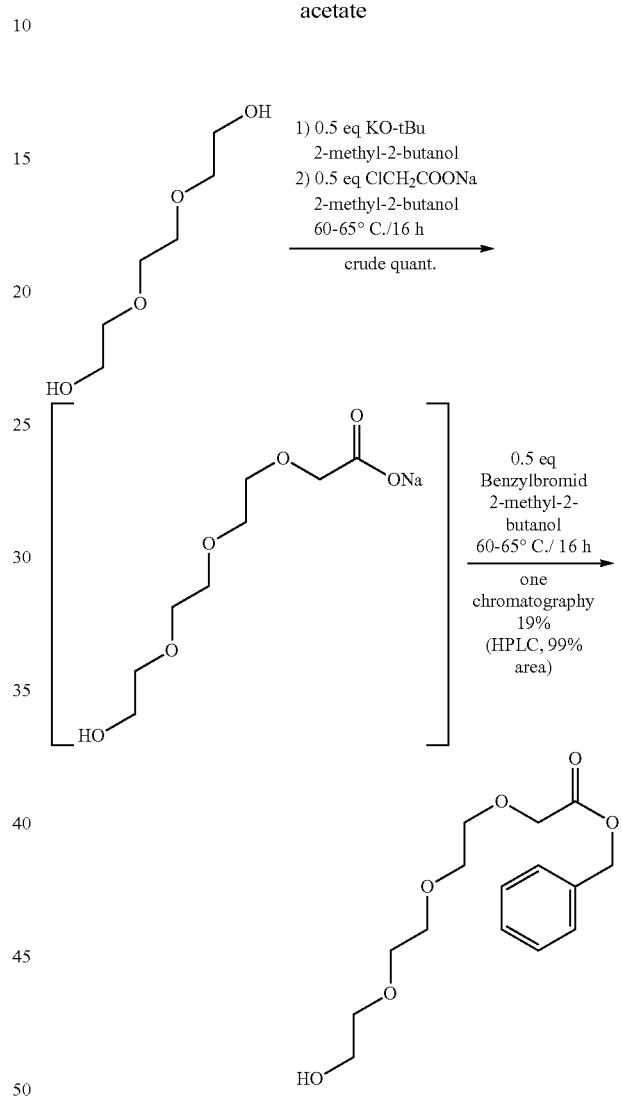

11.2 g potassium tert.-butylate (100.0 mmol, 0.5 eq) was suspended in 70 ml 2-methyl-2-butanol (light exothermic 35° C.), then 30.0 g (200.0 mmol) 2-[2-(2-Hydroxyethoxy)ethoxy]ethanol were added dropwise in the course of 5 min. the dropping funnel were rinsed with 10 ml 2-methyl-2-butanol (temp. increase to 45° C.), the solution was heated to 60-65° C., 11.6 g (100 mmol, 0.5 eq) sodium chloroacetate were added and stirred for 16 h at 60-65° C., then 11.9 ml benzyl bromide (100 mmol, 0.5 eq) were added and the mixture stirred for another 16 h at 60-65° C. The reaction mixture was cooled to rt, then treated with 50 ml water and extracted with 80 ml MTBE and 40 ml MTBE. The combined TBME layer was washed with 50 ml half saturated brine, the organic layer were evaporated at 40° C./300-10 mbar/1 h to obtain crude 27.0 g benzyl 2-[2-[2-(2-hydroxyethoxy)ethoxy]ethoxy]acetate.

After chromatography (270 g silica 60 (0.063-0.2 mm), mobile phase: start with ethyl acetate/n-heptane 1/1, when pure product are visible, mobile phase were changed to 100% ethyl acetate, total 11.4 g benzyl 2-[2-[2-(2-hydroxyethoxy)ethoxy]ethoxy]acetate as nearby colorless oil was isolated in 19% yield (38% from sodium chloroacetate) and 99.0% purity (HPLC area-%).

Example 6

Benzyl 2-[2-[2-[2-[(2R,3R,4R,5R,6R)-3-acetamido-4,5-diacetoxy-6-(acetoxymethyl)tetrahydropyran-2-yl]oxyethoxy]ethoxy]ethoxy]acetate

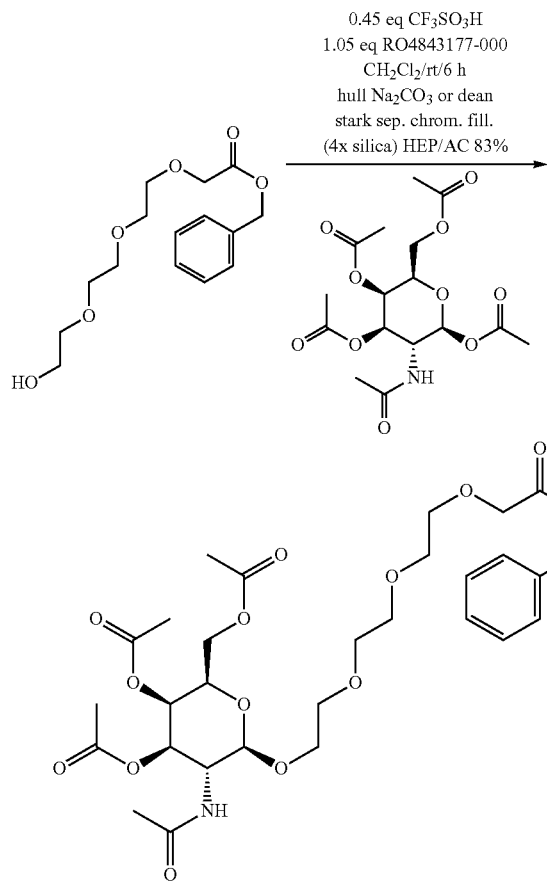

268.0 g Benzyl 2-(2-(2-(2-hydroxyethoxy)ethoxy)ethoxy)acetate (900 mol) were dissolved in 2.4 L dichloromethane. 385.0 g (2S,3R,4R,5R,6R)-3-acetamido-6-(acetoxymethyl)tetrahydro-2H-pyran-2,4,5-triyltriacetate (990 mmol, 1.1 eq) and 12.0 ml trifluoromethanesulfonic acid (135 mmol, 0.15 eq) were added. The suspension was heated to reflux with a dean-stark separator (50 ml, to remove AcOH). After 1 h, 4.50 ml trifluoromethanesulfonic acid (50.7 mmol, 0.05 eq) and 50 ml dichloromethane were added to the orange suspension, the solvent (50 ml) from the dean-stark separator was discharged. Every half hour this procedure was repeated, total 6 times (3 h). After a total of 4.5 h, the red solution was cooled to 10-15° C. and added within 30 min at 20-25° C. to a solution of 1.8 L 1M sodium hydrogen carbonate (1.8 mol, 2.0 eq) ($CO_2$ evolution, pH 7-8). The yellow organic layer was separated and evaporated at 40° C./600-10 mbar/3 h to obtain 585.4 g of crude benzyl 2-[2-[2-[2-[(2R,3R,4R,5R,6R)-3-acetamido-4,5-diacetoxy-6-(acetoxymethyl) tetrahydropyran-2-yl]oxyethoxy]ethoxy]ethoxy]acetate as yellow oil (HPLC purity: 87%). The crude product was dissolved in 700 ml acetone and charged to a preloaded silica column (3.0 kg silica 60; 0.063-0.2 mm). The chromatography was conducted using n-heptane/acetone as mobile phase (gradient from 5:1 to 1:2). The combined collected fractions were evaporated at 40° C./600-10 mbar and dried at 20-25° C./0.3 mbar/3 h to obtain 465.0 g benzyl 2-[2-[2-[2-[(2R,3R,4R,5R,6R)-3-acetamido-4,5-diacetoxy-6-(acetoxymethyl)tetrahydro-pyran-2-yl]oxyethoxy]ethoxy]ethoxy]acetate as yellow oil in 83% yield and 100% purity (HPLC area-%). MS: m/z=628.2627 (M+H)$^+$.

Example 7

2-[2-[2-[2-[(2R,3R,4R,5R,6R)-3-acetamido-4,5-diacetoxy-6-(acetoxymethyl)tetrahydropyran-2-yl]oxyethoxy]ethoxy]ethoxy]acetic acid

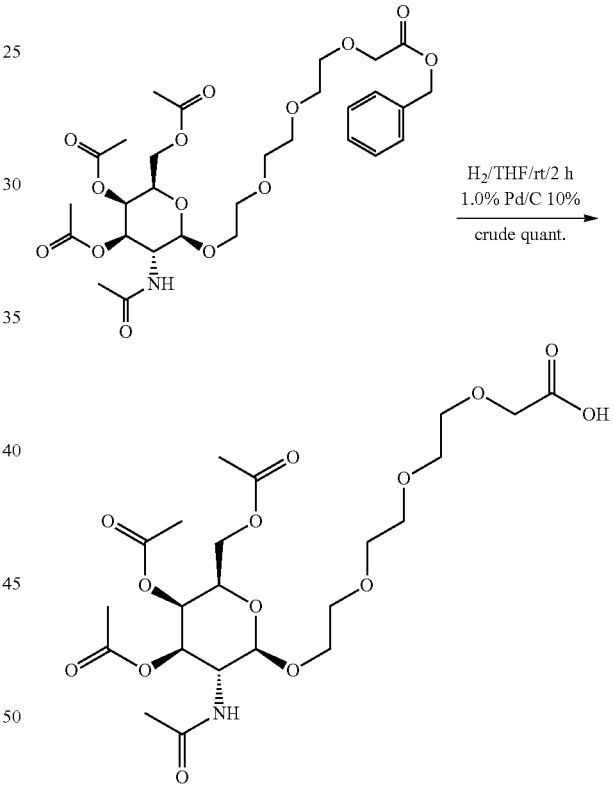

Under argon atmosphere, 456.0 g Benzyl 2-[2-[2-[2-[(2R,3R,4R,5R,6R)-3-acetamido-4,5-diacetoxy-6-(acetoxymethyl)tetrahydro-pyran-2-yl]oxyethoxy]ethoxy]ethoxy]acetate (727 mmol) were dissolved in 1.4 L THF. 4.56 g Pd/C 10% were added and the argon atmosphere was replaced with hydrogen (1 bar). The black suspension was hydrogenated at 20-25° C. for 2 h. The hydrogen atmosphere was replaced with argon, the black suspension was filtered and the filter cake was washed portion-wise with total of 400 ml THF. The colorless filtrate (HPLC purity: 71% and 27% toluene) was used without any purification in the A+B assembly step, example 8. MS: m/z=538.2191 (M+H)$^+$.

Assembly of Building Block A and B:
Example 8
Benzyl (2S)-6-[[2-[2-[2-[2-[(2R,3R,4R,5R,6R)-3-acetamido-4,5-diacetoxy-6-(acetoxymethyl)tetrahydropyran-2-yl]oxyethoxy]ethoxy]ethoxy]acetyl]amino]-2-[[(2S)-2,6-bis[[2-[2-[2-[2-[(2R,3R,4R,5R,6R)-3-acetamido-4,5-diacetoxy-6-(acetoxymethyl)tetrahydropyran-2-yl]oxyethoxy]ethoxy]ethoxy]acetyl]amino]hexanoyl]amino]hexanoate
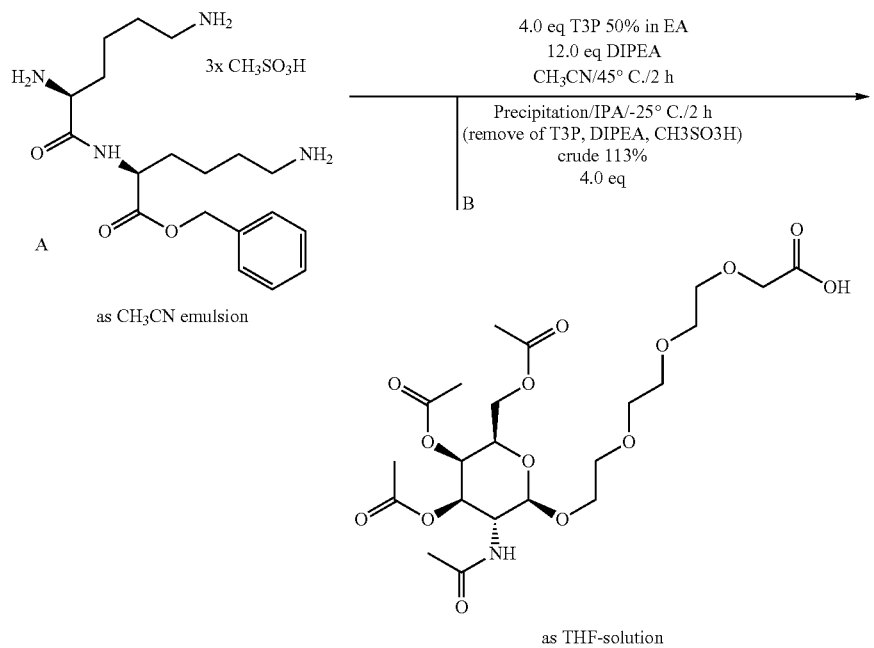
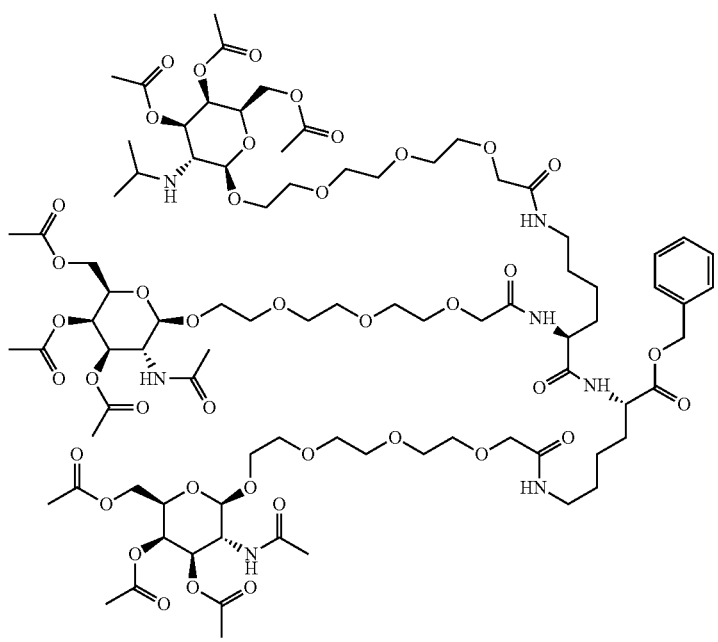

The red-orange solution (~1.4 L) of benzyl (2S)-6-amino-2-[[(2S)-2,6-diaminohexanoyl]amino]hexanoate tri-methanesulfonate (180.0 mmol) from Example 4 was diluted with 3.60 L acetonitrile. At 20-25° C., 365.0 ml N-ethyldiisopropylamine (2.16 mol, 12.0 eq) were added within 5 min. To the formed sticky slurry, a solution (~2.25 L) of 2-[2-[2-[2-[(2R,3R,4R,5R,6R)-3-acetamido-4,5-diacetoxy-6-(acetoxymethyl)tetrahydropyran-2-yl]oxyethoxy]ethoxy]ethoxy]acetic acid (720 mmol, 4.0 eq) from Example 7 was added at 20-25° C. in within 10 min, whereby the temperature slightly increased to 40° C. At 45-50° C., a solution of 425 ml n-propylphosphonic acid anhydride (T3P, trimer 50% in ethyl acetate, 720 mmol, 4.0 eq) was added within 10 min. The reaction solution was stirred for 1 h at 45-50° C. The light yellow solution was cooled to 20-25° C. and evaporated at 40° C./10 mbar/6 h to obtain crude 1.06 kg benzyl (2S)-6-[[2-[2-[2-[2-[(2R,3R,4R,5R,6R)-3-acetamido-4,5-diacetoxy-6-(acetoxymethyl)tetrahydropyran-2-yl]oxyethoxy]ethoxy]ethoxy]acetyl]amino]-2-[[(2S)-2,6-bis[[2-[2-[2-[2-[(2R,3R,4R,5R,6R)-3-acetamido-4,5-diacetoxy-6-(acetoxymethyl) tetrahydropyran-2-yl]oxyethoxy]ethoxy]ethoxy]acetyl]amino]hexanoyl]amino]hexanoate (HPLC purity: 24.1%). The crude product was precipitated in three portions to remove methanesulfonic acid N-ethyldiisopropylamine and residual T3P. 353 g crude product was dissolved in 7.0 L 2-propanol, cooled in 1 h to −25° C., stirred for 1 h at −25° C., filtered over a precooled (−25° C.) G3-glass-filter (no rinse), a part from the precipitated product deposited on the glass-wall from the reactor. All precipitates were dissolved portion-wise from the filter and glass-wall with a total of 1.0 L THF. The combined solutions were evaporated at 40° C./20 mbar/6 h to obtain 390.0 g benzyl (2S)-6-[[2-[2-[2-[2-[(2R,3R,4R,5R,6R)-3-acetamido-4,5-diacetoxy-6-(acetoxymethyl)tetrahydropyran-2-yl]oxyethoxy]ethoxy]ethoxy]acetyl]amino]-2-[[(2S)-2,6-bis[[2-[2-[2-[2-[(2R,3R,4R,5R,6R)-3-acetamido-4,5-diacetoxy-6-(acetoxymethyl)tetrahydropyran-2-yl]oxyethoxy]ethoxy]ethoxy]acetyl]amino]hexanoyl]amino]hexanoate (HPLC purity: 71.9%), which was used without further purification in the next step. MS: m/z=1923.8438 (M+H)$^+$.

Synthesis of the GalNAc Phosphoramidite.

Example 9

(2S)-6-[[2-[2-[2[2-[(2R,3R,4R,5R,6R)-3-acetamido-4,5-diacetoxy-6-(acetoxymethyl)tetrahydropyran-2-yl]oxyethoxy]ethoxy]ethoxy]acetyl]amino]-2-[[(2S)-2,6-bis[[2-[2-[2-[2-[(2R,3R,4R,5R,6R)-3-acetamido-4,5-diacetoxy-6-(acetoxymethyl) tetrahydropyran-2-yl]oxyethoxy]ethoxy]ethoxy]acetyl]amino]hexanoyl]amino]hexanoic acid

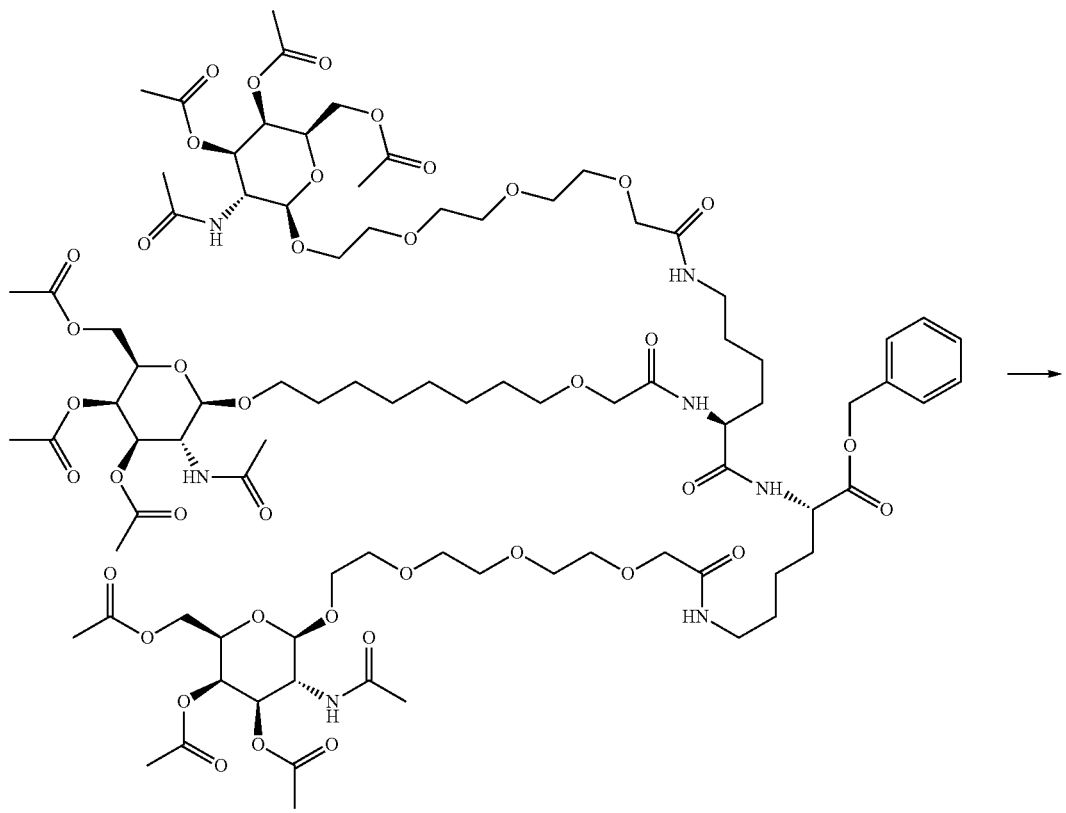

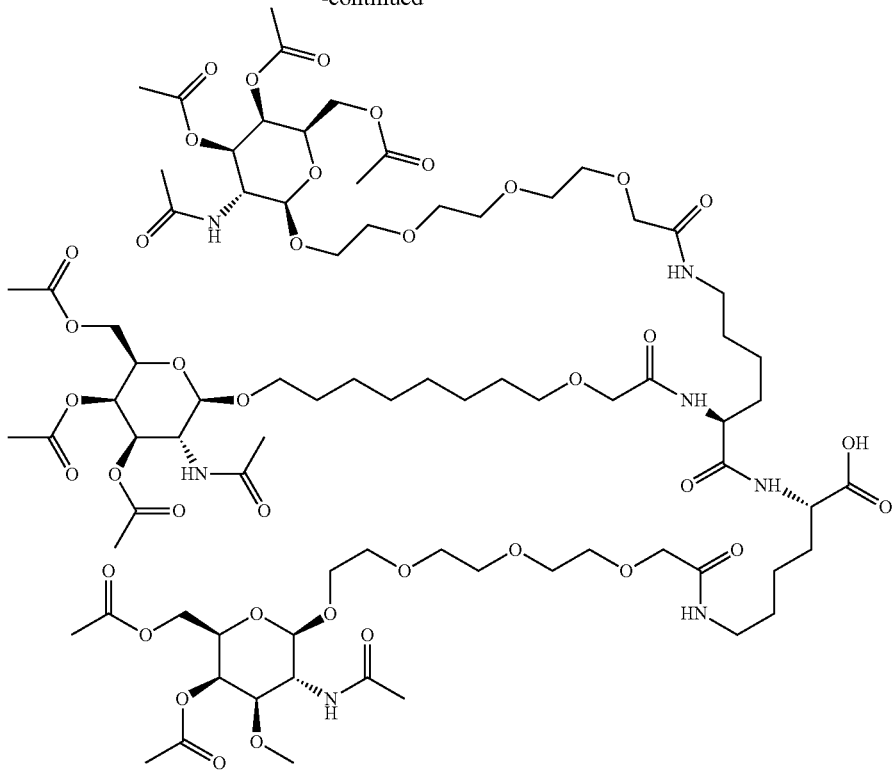

5.0 g (2.6 mmol) benzyl (2S)-6-[[2-[2-[2-[2-[(2R,3R,4R,5R,6R)-3-acetamido-4,5-diacetoxy-6-(acetoxymethyl)tetrahydropyran-2-yl]oxyethoxy]ethoxy]ethoxy]acetyl]amino]-2-[[(2S)-2,6-bis[[2-[2-[2-[2-[(2R,3R,4R,5R,6R)-3-acetamido-4,5-diacetoxy-6-(acetoxymethyl)tetrahydropyran-2-yl]oxyethoxy]ethoxy]ethoxy]acetyl]amino]hexanoyl]amino]hexanoate was dissolved in 25.0 ml THF, 100 mg Pd/C 10% were added, the mixture was flushed three times with argon and then three times with hydrogen gas. The black suspension was hydrogenated at 20-25° C. for 3.0 h under hydrogen atmosphere. The suspension were filtered over a glass fiber filter and the filtrate were evaporated at 20° C./100-10 mbar/1 h to obtain 4.5 g (2S)-6-[[2-[2-[2-[2-[(2R,3R,4R,5R,6R)-3-acetamido-4,5-diacetoxy-6-(acetoxymethyl)tetrahydropyran-2-yl]oxyethoxy]ethoxy]ethoxy]acetyl]amino]-2-[[(2S)-2,6-bis[[2-[2-[2-[2-[(2R,3R,4R,5R,6R)-3-acetamido-4,5-diacetoxy-6-(acetoxymethyl)tetrahydropyran-2-yl]oxyethoxy]ethoxy]ethoxy]acetyl]amino]hexanoyl]amino]hexanoic acid, as light yellow oil. LC-MS, (ESI) MH$^+$ 1832.7941.

Example 10a 2-(6-benzyloxyhexyl)isoindoline-1,3-dione

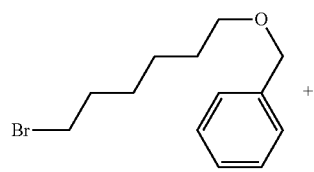

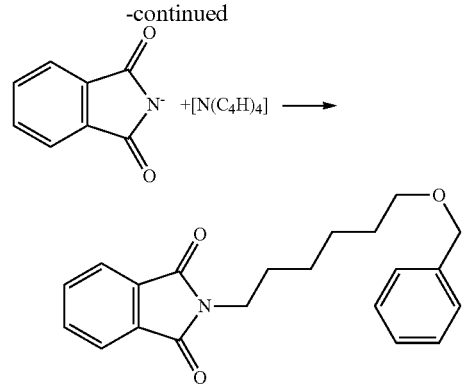

10.8 g (40 mmol) 6-bromohexoxymethylbenzene was dissolved in 55.0 ml THF, 17.1 g 44.0 mmol, 1.1 eq) tetrabutylammonium 1,3-dioxoisoindolin-2-ide (phthalimde/tetrabutyl ammonium hydroxide 25% in methanol 1/1/evaporation/azeotrop with toluene and dried at 40° C.) was added to the colorless solution (light exothermic). The reaction mixture was stirred for 2 h at 20-25° C., the formed suspension was filtered and the filter cake were washed with 20.0 ml THF, the combined filtrate were diluted with 50 ml MTBE and extracted with 50 ml water, the organic layer were separated and dried with anhydrous sodium sulfate, filtered, washed with 30 ml MTBE and evaporated at 40° C./400-15 mbar/3 h to obtain crude 12.9 g 2-(6-benzyloxyhexyl)isoindoline-1,3-dione as light yellow solid, which was used without further purification in the step 10c. MS: m/z=(M+H)$^+$338.1752.

Example 10b

2-(6-benzyloxyhexyl)isoindoline-1,3-dione 12.7 g (47 mmol) 6-bromohexoxymethylbenzene was dissolved in 64.0 ml THF, 9.6 g 51.7 mmol, 1.1 eq) potassium-isoindolin-2-ide-1,3-dione and 0.32 g (0.94 mmol, 0.02 eq) tetrabutylammonium hydrogensulfate was added to the colorless solution. The reaction mixture was refluxed for 18 h, diluted with 64 ml MTBE extracted twice with 64 ml water, the organic layer were separated and dried with anhydrous sodium sulfate, filtered, washed with 30 ml MTBE and evaporated at 40° C./400-15 mbar/3 h to obtain crude 14.7 g 2-(6-benzyloxyhexyl)isoindoline-1,3-dione as off white solid. 10.6 g of crude was treated with a mixture of 37 ml methanol and 5.5 ml water, heated to reflux, after 5 min the cloudy solution was cooled to 20-25° C. and stirred for 1 hour at 20-25° C., the white suspension was filtered and the filter cake were washed with a mixture of 7.0 ml methanol and 1.0 ml water. The white crystals were dried at 40° C./15 mbar/1 h to obtain 9.6 g 2-(6-(benzyloxy)hexyl)isoindoline-1,3-dione as white crystals. MS: m/z=(M+H)$^+$ 338.1752.

Example 10c

6-benzyloxyhexan-1-amine

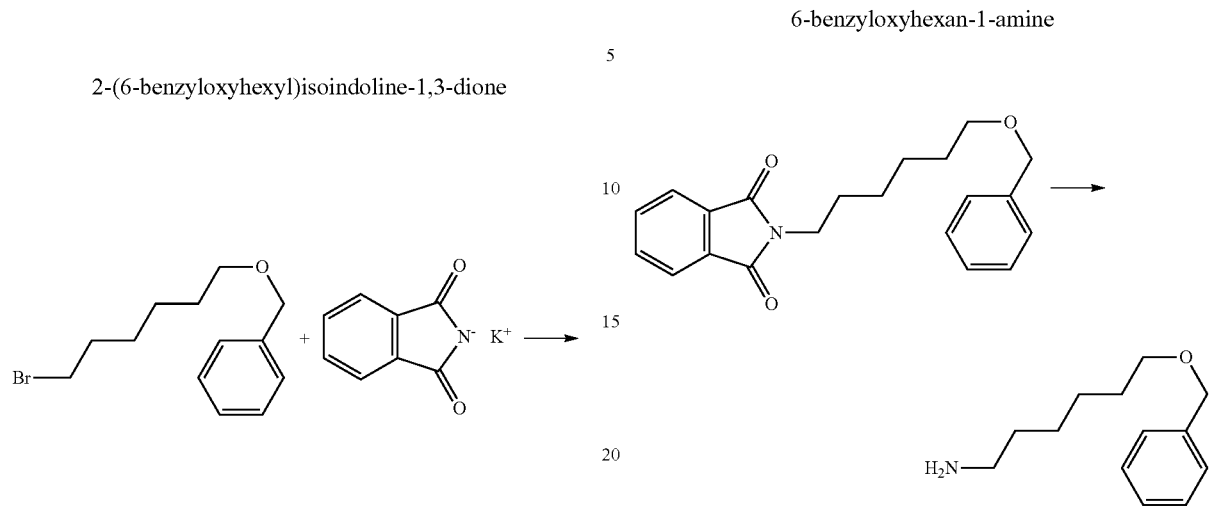

12.8 g (37.9 mmol) 2-(6-(benzyloxy)hexyl)isoindoline-1,3-dione was dissolved in 40.0 ml THF, at room temperature 5.5 ml (113 mmol, 3.0 eq) hydrazine monohydrate 64% in water were added. The colorless solution was heated to 50-55° C. for 2 hour, the formed white suspension were cooled to room temperature and filtered and the white filter cake were washed with total 30.0 ml THF. The filtrate was diluted with 60.0 ml MTBE and extracted with 50 ml water. The organic layer were separated, dried with anhydrous sodium sulfate, filtered and evaporated at 40° C./350-15 mbar/2 h to obtain crude 6.44 g 6-benzyloxyhexan-1-amine as colorless oil.

Formation of hydrochloride salt: 6.44 g (31.1 mmol) were dissolved in 32.0 ml methanol, at room temperature 7.80 ml 4M HCl in methanol were added, the light yellow solution were evaporated at 40° C./150-15 mbar/15 min to obtain crude 8.1 gas yellow oil. To this oil 65.0 ml ethyl acetate were added, were by a white suspension was formed, which were stirred for 16 hour at room temperature. The white suspension were filtered, the filter cake were washed with total 40.0 ml ethyl acetate and dried at 40° C./15 mbar/3 h to obtain 4.95 g 6-benzyloxyhexan-1-amine-hydrochloride as white crystals.

Formation of the free base: 2.0 g 6-benzyloxyhexan-1-amine-hydrochloride were treated with 15.0 ml 1M NaOH/13% NaCl and extracted with 15.0 ml MTBE, the organic layer were separated, dried with anhydrous sodium sulfate, filtered, washed with 5 ml MTBE and evaporated at 40° C./350-15 mbar/2 h to obtain 1.67 g 6-benzyloxyhexan-1-amine as colorless oil. MS: m/z=(M+H)$^+$ 208.17006.

Example 10d

[(2R,3R,4R,5R,6R)-5-acetamido-6-[2-[2-[2-[2-[[(5S)-5-[[2-[2-[2-[2-[(2R,3R,4R,5R,6R)-3-acet-amido-4,5-diacetoxy-6-(acetoxymethyl)tetrahydro-pyran-2-yl]oxyethoxy]ethoxy]ethoxy]acetyl]amino]-6-[[(1S)-5-[[2-[2-[2-[2-[(2R,3R,4R,5R,6R)-3-acetamido-4,5-diacetoxy-6-(acetoxymethyl)tetrahydropyran-2-yl]oxyethoxy]ethoxy]ethoxy]acetyl]amino]-1-(6-benzyloxyhexylcarbamoyl)pentyl]amino]-6-oxo-hexyl]amino]-2-oxo-ethoxy]ethoxy]ethoxy]ethoxy]-3,4-diacetoxy-tetrahydropyran-2-yl]methyl acetate

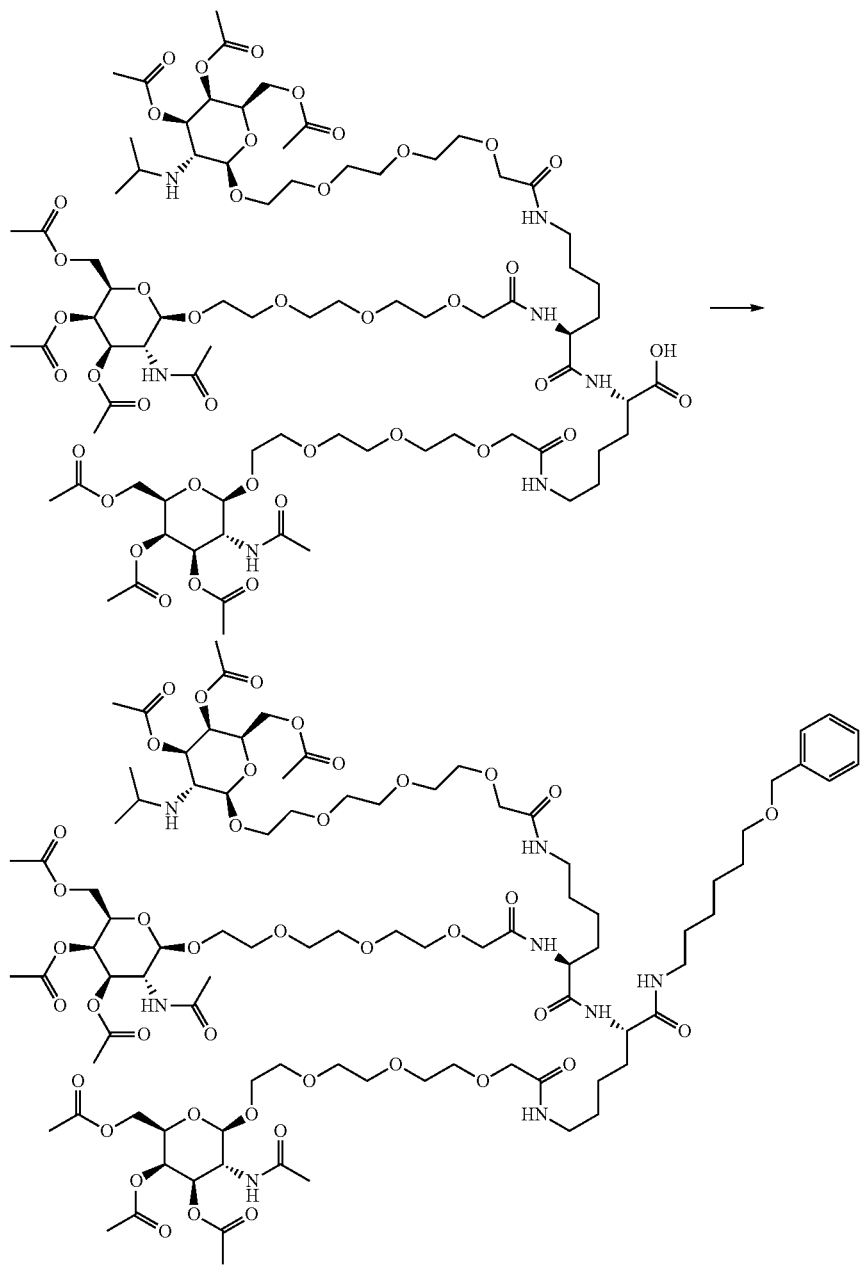

4.4 g (2S)-6-[[2-[2-[2-[2-[(2R,3R,4R,5R,6R)-3-acet-amido-4,5-diacetoxy-6-(acetoxymethyl)tetrahydropyran-2-yl]oxyethoxy]ethoxy]ethoxy]acetyl]amino]-2-[[(2S)-2,6-bis [[2-[2-[2-[2-[(2R,3R,4R,5R,6R)-3-acetamido-4,5-diacetoxy-6-(acetoxymethyl) tetrahydropyran-2-yl]oxyethoxy]ethoxy]ethoxy]acetyl]amino]hexanoyl]amino]hexanoic acid was dissolved in 45.0 ml THF, at 20-25° C. 0.55 g (2.64 mmol, 1.1 eq) 6-benzyloxyhexan-1-amine and 1.22 ml (7.2 mmol, 3.0 eq) N-ethyldiisopropylamine were added, the solution was warmed to 35-40° C. and 1.84 ml n-propylphosphonic acid anhydride (T3P as cyclic trimer 50% in ethyl acetate, 3.12 mmol, 1.3 eq) were added to the light yellow solution. The mixture was stirred for 4.0 h at 35-40° C., cooled to 20-25° C. and evaporated at 20-25° C./100-10 mbar/2 h to obtain 6.5 g crude product. The product were purified with SFC/RP-C18/2-propanol to obtain 2.91 g [(2R,3R,4R,5R,6R)-5-acetamido-6-[2-[2-[2-[2-[[(5S)-5-[[2-[2-[2-[2-[(2R,3R,4R,5R,6R)-3-acetamido-4,5-diacetoxy-6-(acetoxymethyl)tetrahydropyran-2-yl]oxyethoxy]ethoxy]ethoxy]acetyl]amino]-6-[[(1S)-5-[[2-[2-[2-[2-[(2R,3R,4R,5R,6R)-3-acetamido-4,5-diacetoxy-6-(acetoxymethyl)tetrahydropyran-2-yl]oxyethoxy]ethoxy]ethoxy]acetyl]amino]-1-(6-benzyloxyhexylcarbamoyl)pentyl]amino]-6-oxo-hexyl]amino]-2-oxo-ethoxy]ethoxy]ethoxy]ethoxy]-3,4-diacetoxy-tetrahydropyran-2-yl]methyl acetate, as white foam. LC-MS, (ESI) MH+ 2021.945.

Example 11

[(2R,3R,4R,5R,6R)-5-acetamido-6-[2-[2-[2-[2-[[(5S)-5-[[2-[2-[2-[2-[(2R,3R,4R,5R,6R)-3-acetamido-4,5-diacetoxy-6-(acetoxymethyl)tetrahydropyran-2-yl]oxyethoxy]ethoxy]ethoxy]acetyl]amino]-6-[[(1S)-5-[[2-[2-[2-[2-[(2R,3R,4R,5R,6R)-3-acetamido-4,5-diacetoxy-6-(acetoxymethyl)tetrahydropyran-2-yl]oxyethoxy]ethoxy]ethoxy]acetyl]amino]-1-(6-hydroxyhexylcarbamoyl)pentyl]amino]-6-oxo-hexyl]amino]-2-oxo-ethoxy]ethoxy]ethoxy]ethoxy]-3,4-diacetoxy-tetrahydropyran-2-yl]methyl acetate

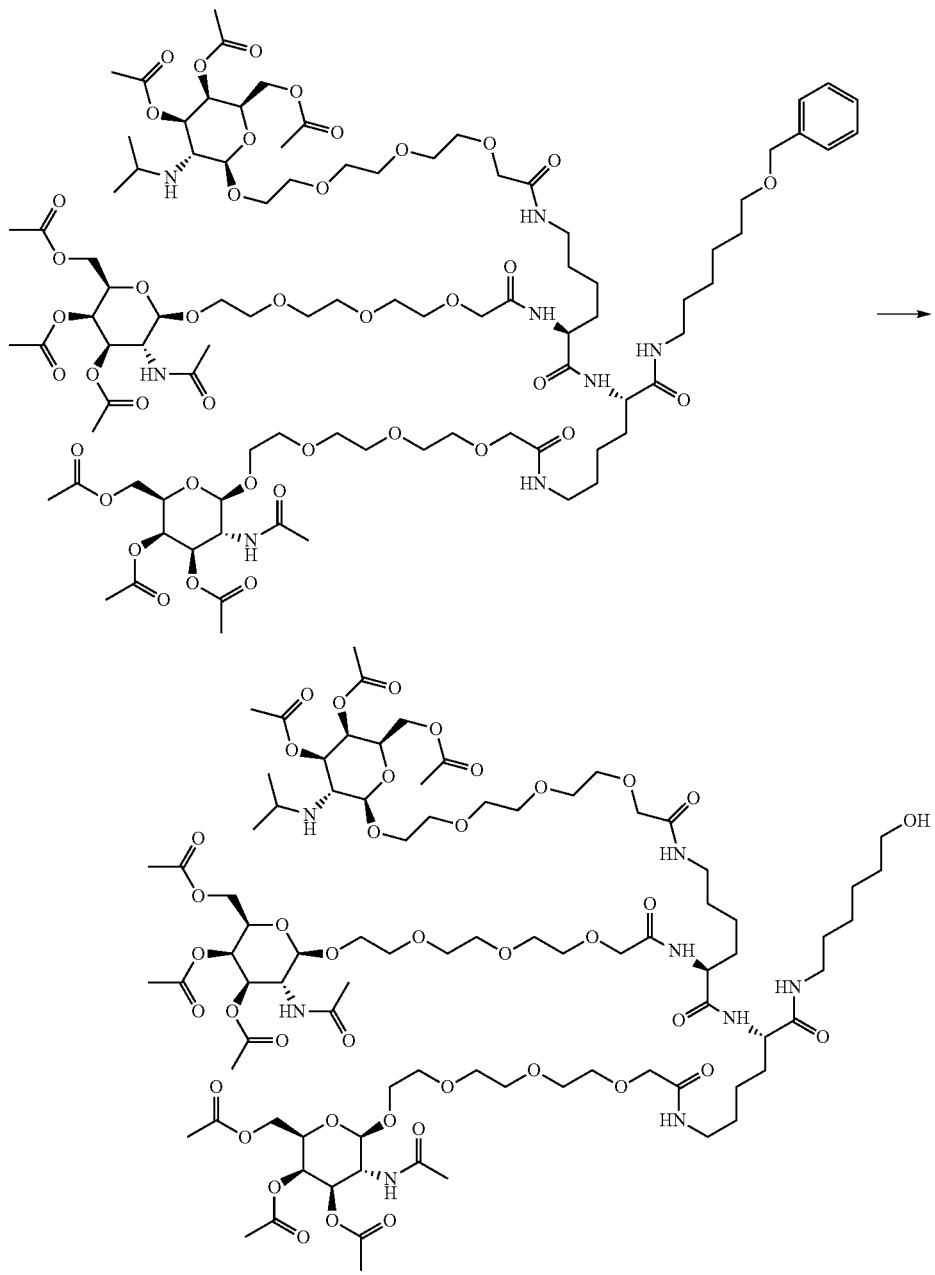

1.62 g (0.80 mmol) [(2R,3R,4R,5R,6R)-5-acetamido-6-[2-[2-[2-[2-[[(5S)-5-[[2-[2-[2-[2-[(2R,3R,4R,5R,6R)-3-acetamido-4,5-diacetoxy-6-(acetoxymethyl)tetrahydropyran-2-yl]oxyethoxy]ethoxy]ethoxy]acetyl]amino]-6-[[(1S)-5-[[2-[2-[2-[2-[(2R,3R,4R,5R,6R)-3-acetamido-4,5-diacetoxy-6-(acetoxymethyl)tetrahydropyran-2-yl]oxyethoxy]ethoxy]ethoxy]acetyl]amino]-1-(6-benzyloxyhexylcarbamoyl)pentyl]amino]-6-oxo-hexyl]amino]-2-oxo-ethoxy]ethoxy]ethoxy]-3,4-diacetoxy-tetrahydropyran-2-yl]methyl acetate were dissolved in 8.0 ml methanol, 162 mg Pd/C 10% were added, the mixture was flushed three times with first argon and then three times with hydrogen gas, The black suspension was hydrogenated at 20-25° C. for 1.5 hour, The black suspension were filtered over a glass fiber filter, the colorless filtrate were evaporated at 20° C./100-10 mbar/1 h. The colorless oil was solved in 10 ml acetonitrile and evaporated at 100-10 mbar/1 h and treated again with 10 ml acetonitrile and evaporated at 100-10 mbar/1 h, the colorless oil were then dried at 20-25° C. at 1 mbar for 2 h to obtain 1.50 g [(2R,3R,4R,5R,6R)-5-acetamido-6-[2-[2-[2-[2-[[(5S)-5-[[2-[2-[2-[2-[(2R,3R,4R,5R,6R)-3-acetamido-4,5-diacetoxy-6-(acetoxymethyl)tetrahydropyran-2-yl]oxyethoxy]ethoxy]ethoxy]acetyl]amino]-6-[[(1S)-5-[[2-[2-[2-[2-[(2R,3R,4R,5R,6R)-3-acetamido-4,5-diacetoxy-6-(acetoxymethyl)tetrahydropyran-2-yl]oxyethoxy]ethoxy]ethoxy]acetyl]amino]-1-(6-hydroxyhexylcarbamoyl)pentyl]amino]-6-oxo-hexyl]amino]-2-oxo-ethoxy]ethoxy]ethoxy]-3,4-diacetoxy-tetrahydropyran-2-yl]methyl acetate, as colorless oil. LC-MS MH$^+$ 1931.90142.

Example 12

[(2R,3R,4R,5R,6R)-5-acetamido-6-[2-[2-[2-[2-[[(5S)-5-[[2-[2-[2-[2-[(2R,3R,4R,5R,6R)-3-acetamido-4,5-diacetoxy-6-(acetoxymethyl)tetrahydropyran-2-yl]oxyethoxy]ethoxy]acetyl]amino]-6-[[(1S)-5-[[2-[2-[2-[2-[(2R,3R,4R,5R,6R)-3-acetamido-4,5-diacetoxy-6-(acetoxymethyl)tetrahydropyran-2-yl]oxyethoxy]ethoxy]ethoxy]acetyl]amino]-1-[6-[2-cyanoethoxy-(diisopropylamino)phosphanyl]oxyhexylcarbamoyl]pentyl]amino]-6-oxo-hexyl]amino]-2-oxo-ethoxy]ethoxy]ethoxy]ethoxy]-3,4-diacetoxy-tetrahydropyran-2-yl]methyl acetate.

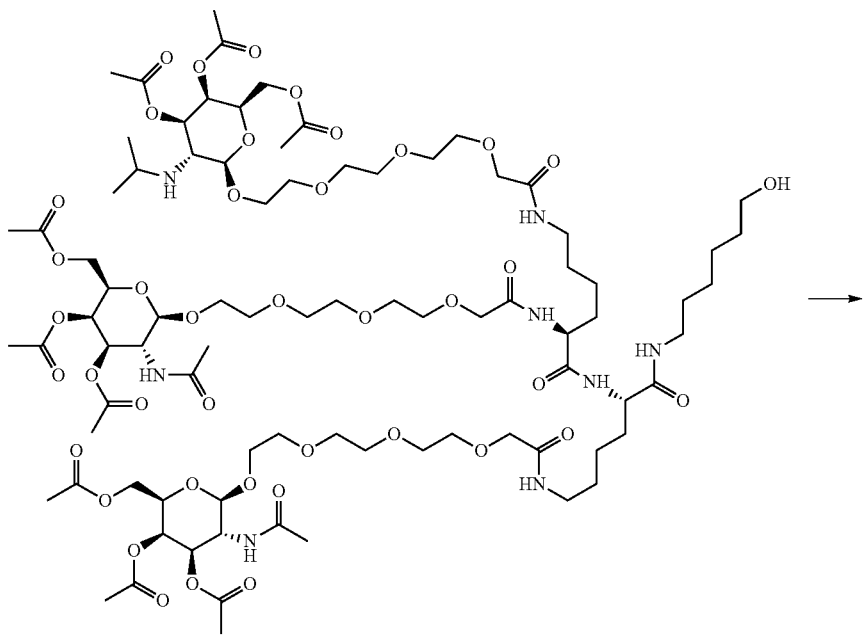

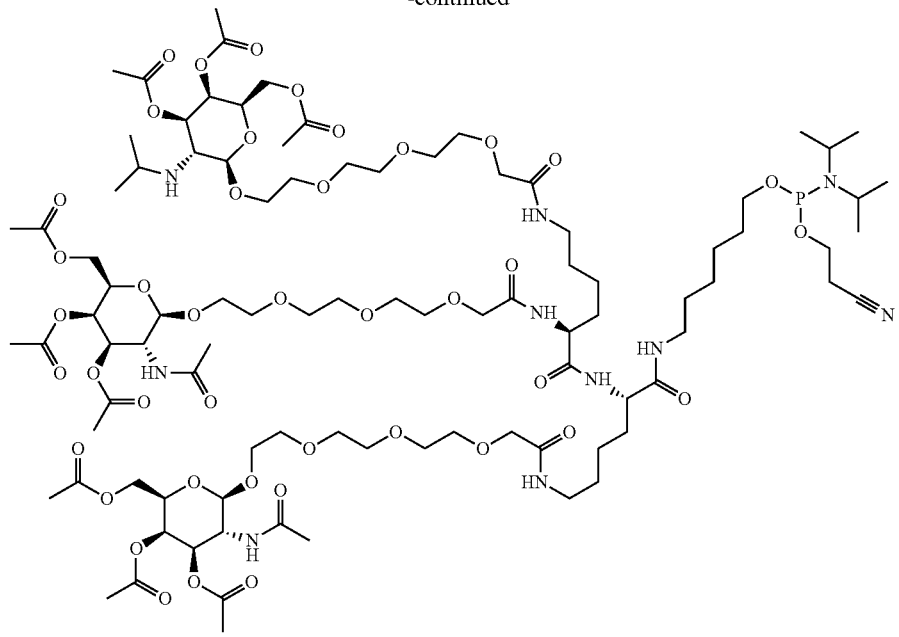

1.50 g (0.77 mmol) [(2R,3R,4R,5R,6R)-5-acetamido-6-[2-[2-[2-[2-[[(5S)-5-[[2-[2-[2-[2-[(2R,3R,4R,5R,6R)-3-acetamido-4,5-diacetoxy-6-(acetoxymethyl)tetrahydropyran-2-yl]oxyethoxy]ethoxy]ethoxy]acetyl]amino]-6-[[(1S)-5-[[2-[2-[2-[2-[(2R,3R,4R,5R,6R)-3-acetamido-4,5-diacetoxy-6-(acetoxymethyl)tetrahydropyran-2-yl]oxyethoxy]ethoxy]ethoxy]acetyl]amino]-1-(6-hydroxyhexylcarbamoyl)pentyl]amino]-6-oxo-hexyl]amino]-2-oxo-ethoxy]ethoxy]ethoxy]-3,4-diacetoxy-tetrahydropyran-2-yl]methyl acetate were dissolved in 5.0 ml acetonitrile, the light yellow solution were cooled to 0-5° C., 0.184 ml triethylamine and 2-cyanoethyl-N,N-diisopropylchlorophosphoramidite were added at 0-5° C. After 15 min 1.50 g molecular sieves 3A beads 4-8 mesh were added and stirred at 0-5° C. for 10 min, the suspension were filtered over a glass fiber filter and the light yellow solution was evaporated at 20-25° C./100-10 mbar/0.5 h to obtain 1.50 g [(2R,3R,4R,5R,6R)-5-acetamido-6-[2-[2-[2-[2-[[(5S)-5-[[2-[2-[2-[2-[(2R,3R,4R,5R,6R)-3-acetamido-4,5-diacetoxy-6-(acetoxymethyl)tetrahydropyran-2-yl]oxyethoxy]ethoxy]ethoxy]acetyl]amino]-6-[[(1S)-5-[[2-[2-[2-[2-[(2R,3R,4R,5R,6R)-3-acetamido-4,5-diacetoxy-6-(acetoxymethyl) tetrahydropyran-2-yl]oxyethoxy]ethoxy]ethoxy]acetyl]amino]-1-[6-[2-cyanoethoxy-(diisopropylamino)phosphanyl]oxyhexylcarbamoyl]pentyl]amino]-6-oxo-hexyl]amino]-2-oxo-ethoxy]ethoxy]ethoxy]-3,4-diacetoxy-tetrahydropyran-2-yl]methyl acetate, as yellow oil, which were used in the next step without further purification. $^{31}$P-NMR DMSO-d$^6$ 146.33 ppm (s 1P). LC-MS, M(NH$_4$)$^+$ 2149.0.

Example 13

Hexadecaammonium; [(3S)-2-[[6-[[6-[[2-[2-[2-[2-[(2R)-3-acetamido-4,5-dihydroxy-6-(hydroxymethyl)tetrahydropyran-2-yl]oxyethoxy]ethoxy]ethoxy]acetyl]amino]-2-[2,6-bis[[2-[2-[2-[2-[(2R)-3-acetamido-4,5-dihydroxy-6-(hydroxymethyl)tetrahydropyran-2-yl]oxyethoxy]ethoxy]ethoxy]acetyl]amino]hexanoylamino]hexanoyl]amino]hexoxy-oxido-phosphoryl]oxymethyl]-5-(4-amino-2-oxo-pyrimidin-1-yl)tetrahydrofuran-3-yl][(2R,3 S,5R)-3-[[(1R,4R,6R,7S)-7-[[(1R,4R,6R,7S)-6-(4-amino-5-methyl-2-oxo-pyrimidin-1-yl)-7-[[(1R,4R,6R,7S)-6-(2-amino-6-oxo-1H-purin-9-yl)-7-[[(2R,3 S,5R)-3-[[(2R,3 S,5R)-3-[[(2R,3 S,5R)-3-[[(2R,3 S,5R)-3-[[(2R,3 S,5R)-5-(2-amino-6-oxo-1H-purin-9-yl)-3-[[(2R,3 S,5R)-3-[[(2R,3 S,5R)-5-(2-amino-6-oxo-1H-purin-9-yl)-3-[[(2R,3 S,5R)-3-[[(4R)-6-(2-amino-6-oxo-1H-purin-9-yl)-7-[[6-(2-amino-6-oxo-1H-purin-9-yl)-7-[[7-hydroxy-6-(5-methyl-2,4-dioxo-pyrimidin-1-yl)-2,5-dioxabicyclo[2.2.1]heptan-4-yl]methoxy-oxido-phosphinothioyl]oxy-2,5-dioxabicyclo[2.2.1]heptan-4-yl]methoxy-oxido-phosphinothioyl]oxy-2,5-dioxabicyclo[2.2.1]heptan-4-yl]methoxy-oxido-phosphinothioyl]oxy-5-(6-aminopurin-9-yl)tetrahydrofuran-2-yl]methoxy-oxido-phosphinothioyl]oxy-tetrahydrofuran-2-yl]methoxy-oxido-phosphinothioyl]oxy-5-(6-aminopurin-9-yl)tetrahydrofuran-2-yl]methoxy-oxido-phosphinothioyl]oxy-tetrahydrofuran-2-yl]methoxy-oxido-phosphinothioyl]oxy-5-(6-aminopurin-9-yl)tetrahydrofuran-2-yl]methoxy-oxido-phosphinothioyl]oxy-5-(6-aminopurin-9-yl)tetrahydrofuran-2-yl]methoxy-oxido-phosphinothioyl]oxy-5-(6-aminopurin-9-yl)tetrahydrofuran-2-yl]methoxy-oxido-phosphinothioyl]oxy-5-(5-methyl-2,4-dioxo-pyrimidin-1-yl)tetrahydrofuran-2-yl]methoxy-oxido-phosphinothioyl]oxy-2,5-dioxabicyclo[2.2.1]heptan-4-yl]methoxy-oxido-phosphinothioyl]oxy-2,5-dioxabicyclo[2.2.1]heptan-4-yl]methoxy-oxido-phosphinothioyl]oxy-6-(2-amino-6-oxo-1H-purin-9-yl)-2,5-dioxabicyclo[2.2.1]heptan-4-yl]methoxy-oxido-phosphoryl]oxy-5-(6-aminopurin-9-yl)tetrahydrofuran-2-yl]methyl phosphate

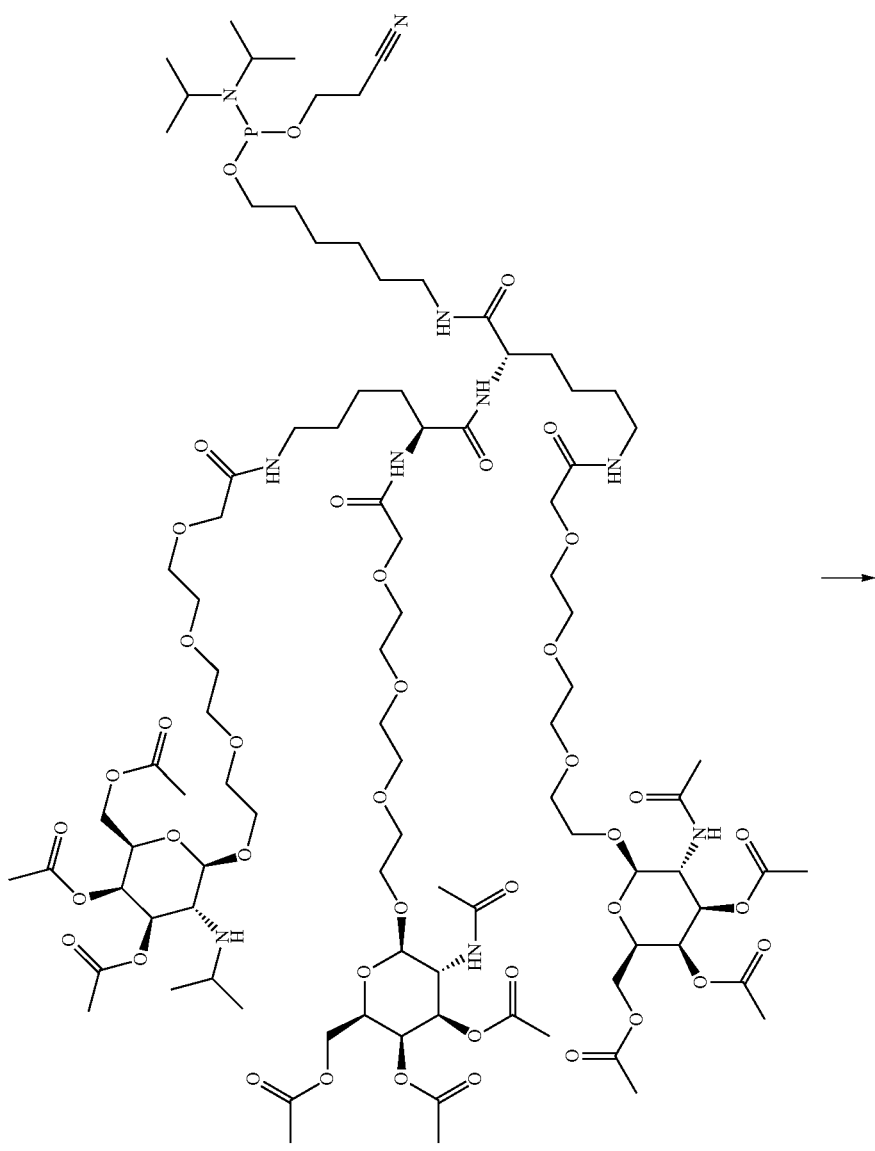

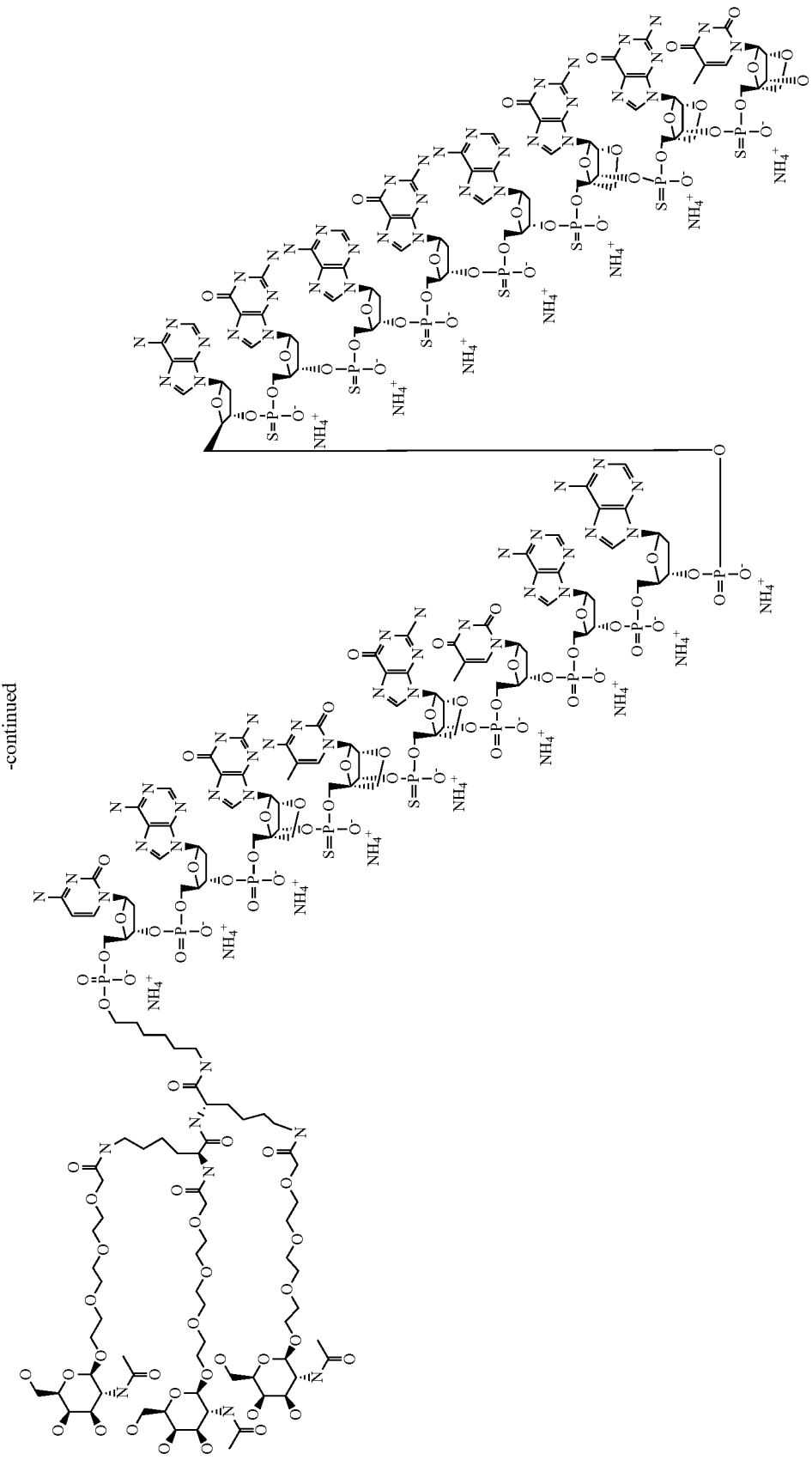

GalNAc-cluster-modified LNA/DNA was produced by standard phosphoramidite chemistry on solid phase at a scale of 0.200 mmol using an AKTA Oligopilot 100 (GE Healthcare, Freiburg, Germany and Primer Support 5G Unylinker 350 (GE Healthcare, Freiburg, Germany). LNA containing, 2'-OCH$_2$-4' bridged nucleotides (Sigma-Aldrich, SAFC, Hamburg, Germany) and DNA (Sigma-Aldrich, SAFC, Hamburg, Germany) were generated employing the corresponding phosphoramidite and GalNAc-cluster phosphoramidite. Cleavage and deprotection was achieved by methods known in the field (Wincott F. et al. Nucleic Acid Research, 1995, 23, 14, 2677-84). The deprotected and dried crude GalNAc-cluster modified LNA as ammonium salt (1.6 g) was characterized and the identity was confirmed with ion pair HPLC-MS to be:

(COMP NO 2)

GNalNAc-cluster-AM-C6-5'-caG$_S$$^m$C$_S$G$_S$t$_S$a$_S$a$_S$a$_S$g$_S$a$_S$g$_S$a$_S$G$_S$G$_S$T-3';

$C_{231}H_{316}N_{78}O_{118}P_{16}S_{13}$, LC-MS, M (ESI) 6981.3.

(Uppercase letters denote beta-D-oxy-LNA units; lowercase letters denote DNA units; the subscript "s" denotes a phosphorothioate linkage; superscript m denotes a DNA or beta-D-oxy-LNA unit containing a 5-methylcytosine base and AM-C6 denote a 6-aminohexyl-1-phosphate linkage)

What is claimed is:

1. A GalNAc phosphoramidite derivative comprising formula I:

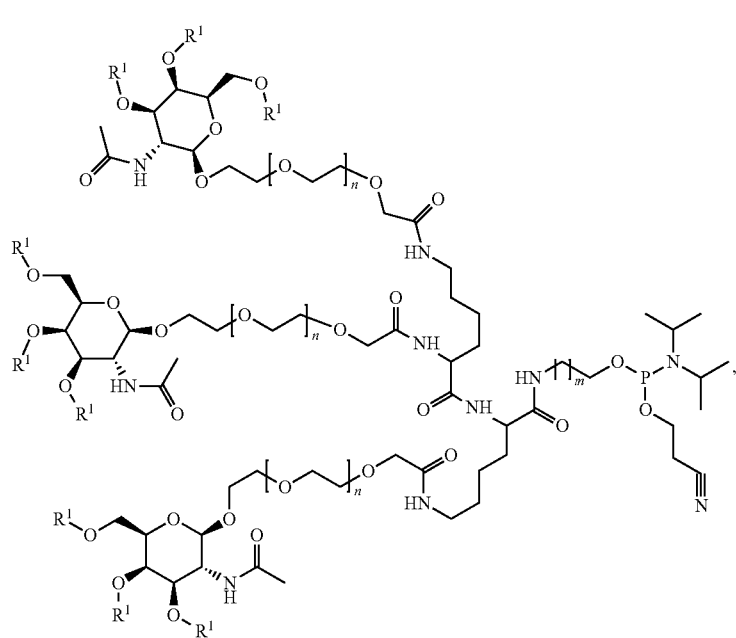

wherein,

R$^1$ is a hydroxy protecting group;

n is an integer from 0 to 10; and m is an integer from 0 to 20;

or an enantiomer or optical isomer thereof.

2. The GalNAc phosphoramidite derivative of claim 1, wherein R$^1$ is an acyl group.

3. The GalNAc phosphoramidite derivative of claim 1, wherein R$^1$ is a $C_{1-6}$-alkylcarbonyl group optionally substituted by $C_{1-6}$-alkyl or phenyl.

4. The GalNAc phosphoramidite derivative of claim 1, wherein n is an integer from 0 to 5 and m is an integer from 0 to 10.

5. The GalNAc phosphoramidite derivative of claim 1, of the formula Ia:

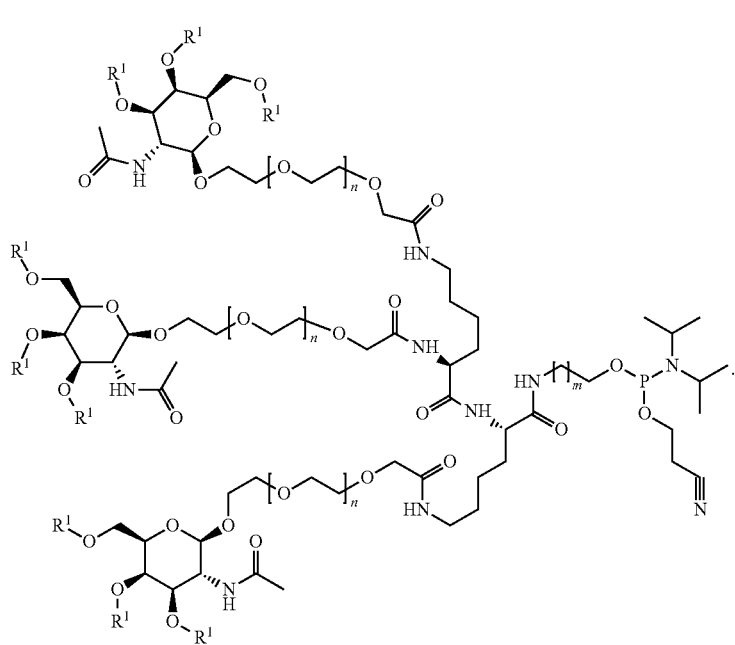
(Ia)
6. The GalNAc phosphoramidite derivative of claim 1, wherein $R^1$ is acetyl, n is 2, and m is 5.
7. The GalNAc phosphoramidite derivative of claim 1, of the formula Ib:
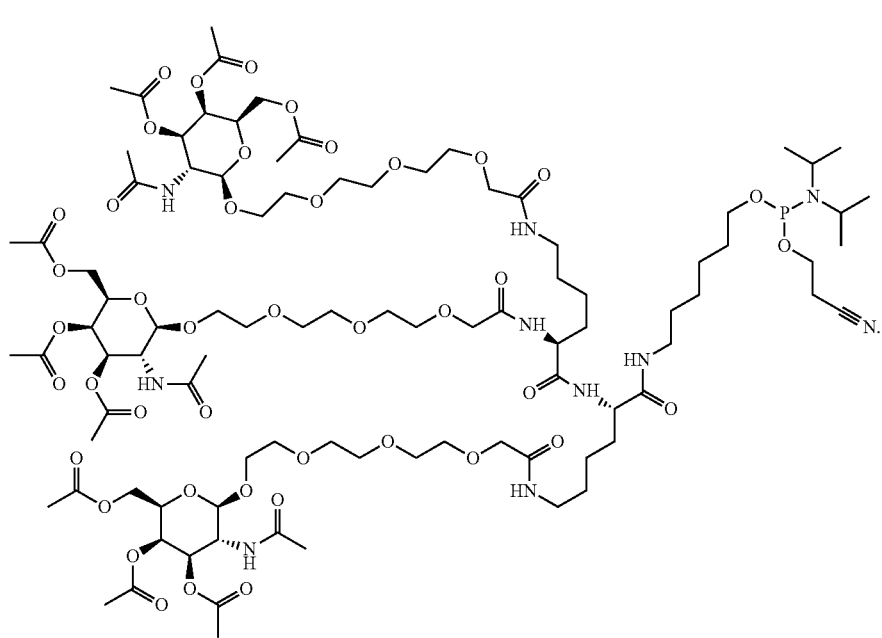
(Ib)

8. A process for the preparation of a GalNAc phosphoramidite derivative of the formula I:
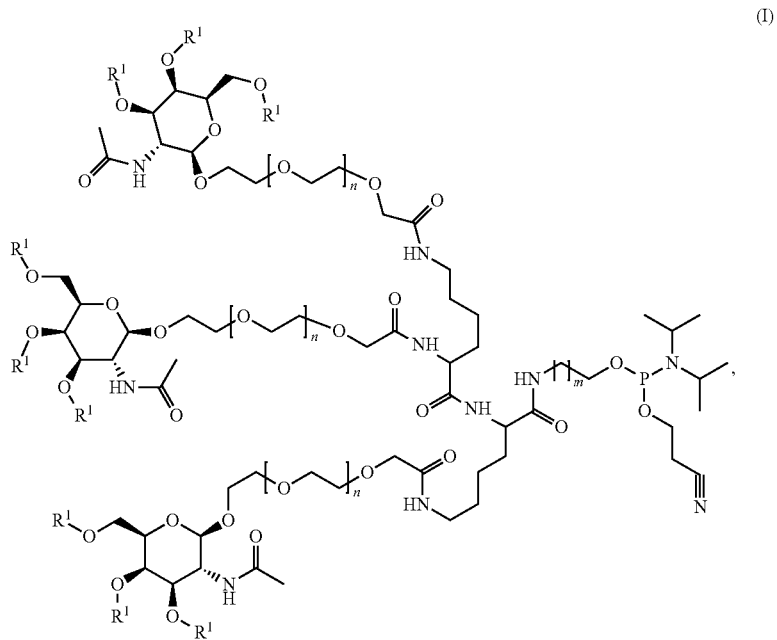
(I)
the process comprising:
a) reacting a GalNAc acid derivative of formula III:
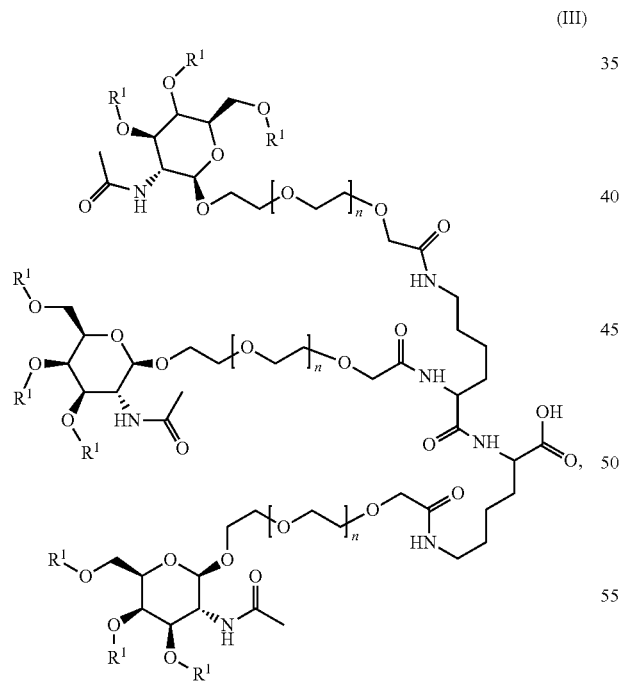
(III)
wherein R$^1$ is a hydroxy protecting group and n is an integer from 0 to 10 with an amine of formula IV:
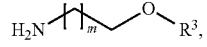
(IV)
wherein R$^3$ is a hydroxy protecting group and m is an integer from 0 to 20, to form an amide of formula V:

(V)

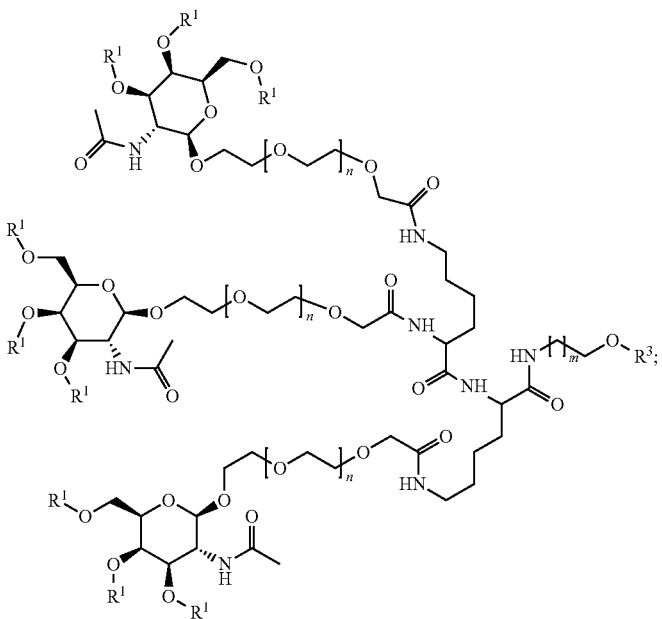

b) removing R³ to form a GalNAc acid amide of formula VI:

(VI)

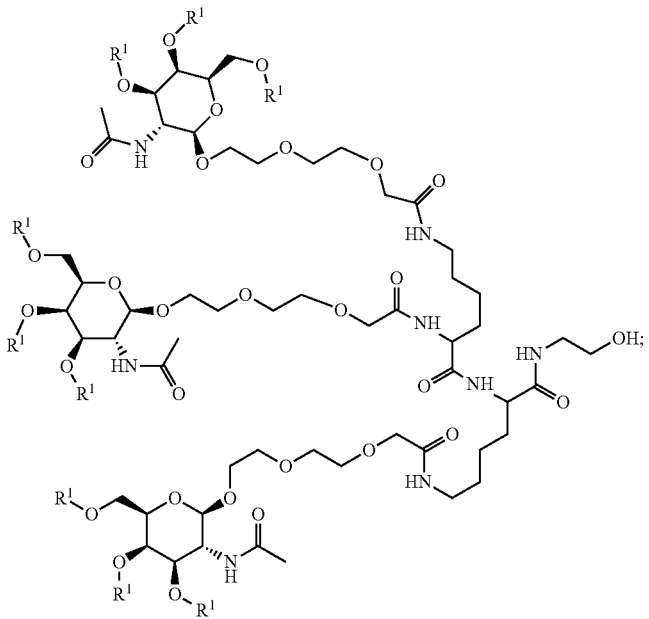

and c) reacting the GalNAc acid amide of formula VI with a phosphoroamidating agent to form the GalNAc phosphoramidite derivative of the formula I.

9. The process of claim 8, wherein the amide formation in step a) is performed in the presence of a peptide coupling agent, an amine base and an organic solvent.

10. The process of claim 9, wherein the peptide coupling agent is n-propylphosphonic acid anhydride, the amine base is a tertiary amine, the organic solvent is a polar aprotic solvent, and the reaction temperature is selected from 20° C. to 70° C.

11. The process of claim 8, wherein the removal of R³ in step b) is performed using hydrogenolysis by way of catalytic hydrogenation with hydrogen in the presence of a hydrogenation catalyst.

12. The process of claim 8, wherein R³ is benzyl.

13. The process of claim 8, wherein the phosphoroamidating agent in step c) is 2-cyanoethyl-N,N-di-(2-propyl) chlorophosphoroamidite or 2-Cyanoethyl-N,N,N',N'-tetra (2-propyl)phosphorodiamidite.

14. The process of claim 8, wherein the reaction in step c) is performed with 2-cyanoethyl-N,N-diisopropylchlorophosphoramidite in the presence of a tertiary amine and a polar aprotic solvent at a reaction temperature between −20° C. and 50° C.

15. A method for preparing a GalNAc-cluster oligonucleotide conjugate, the process comprising the steps of:

a2) preparing a GalNAc phosphoramidite derivative of formula I

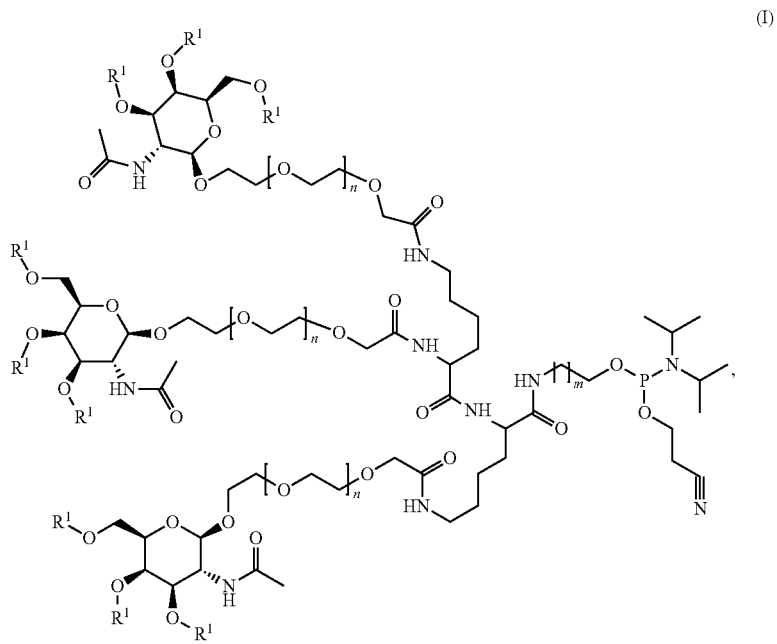

(I)

wherein, $R^1$ is a hydroxy protecting group;

n is an integer from 0 to 10; and m is an integer from 0 to 20;

or an enantiomer or optical isomer thereof, according to claim 8;

b2) contacting the synthesized GalNAc phosphoramidite derivative of step a2 using solid phase oligonucleotide synthesis with a nucleoside building block and repeating the contacting steps with another nucleoside building block to form a GalNAc-cluster oligonucleotide conjugate bound to the solid support; and c2) cleaving and deprotecting the GalNAc-cluster oligonucleotide conjugate of step b2 from the solid phase support thereby forming the GalNAc-cluster oligonucleotide conjugate.

16. The method of claim 15, wherein the GalNAc phosphoramidite derivative comprises a GalNAc phosphoramidite derivative of formula Ia

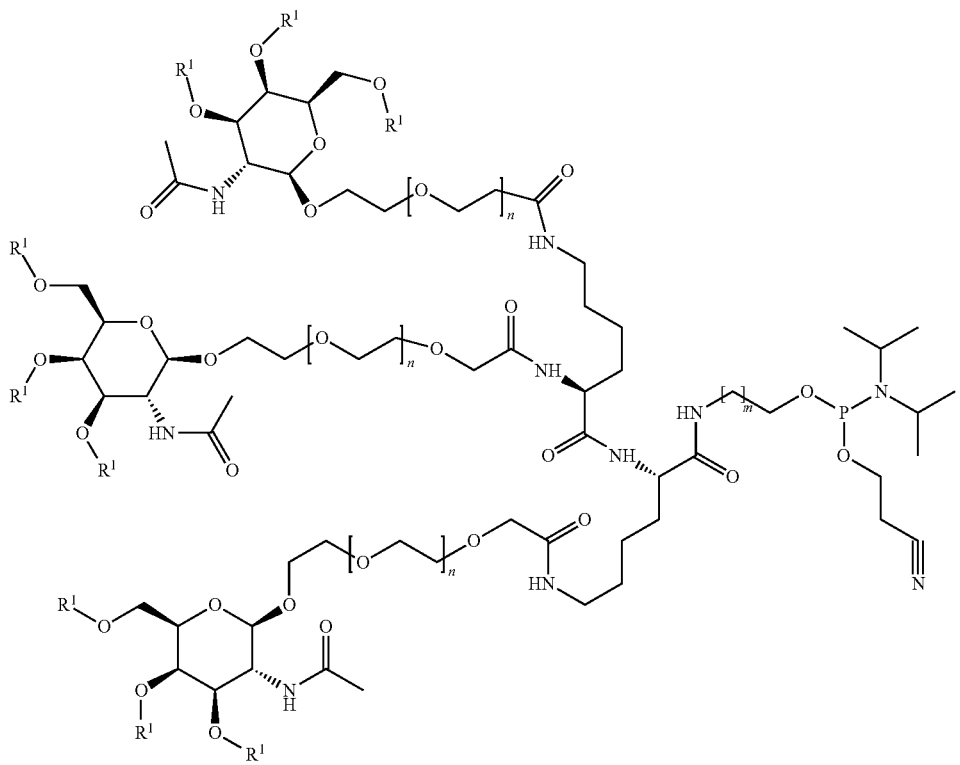

(Ia)

wherein,
$R^1$ is a hydroxy protecting group;
n is an integer from 0 to 10; and
m is an integer from 0 to 20;
or an enantiomer or optical isomer thereof.

17. The method of claim 15, wherein the GalNAc-cluster oligonucleotide conjugate comprises:

(COMP NO 1)
GalNAc-cluster-AM-C6-5'-caG$_S$$^m$C$_S$G$_S$t$_S$a$_S$a$_S$a$_S$g$_S$a$_S$g$_S$a$_S$G$_S$G-3';

(COMP NO 2)
GalNAc-cluster-AM-C6-5'-caG$_S$$^m$C$_S$G$_S$t$_S$a$_S$a$_S$a$_S$g$_S$a$_S$g$_S$a$_S$G$_S$G$_S$T-3';

(COMP NO 3)
GalNAc-cluster-AM-C6-5'-caG$_S$$^m$C$_S$G$_S$t$_S$a$_S$a$_S$a$_S$g$_S$a$_S$g$_S$A$_S$G$_S$G-3';

(COMP NO 4)
GalNAc-cluster-AM-C6-5'-caG$_S$G$_S$$^m$C$_S$G$_S$t$_S$a$_S$a$_S$a$_S$g$_S$a$_S$g$_S$a$_S$G$_S$G-3';

(COMP NO 5)
GalNAc-cluster-AM-C6-5'-caA$_S$G$_S$$^m$C$_S$g$_S$a$_S$a$_S$g$_S$t$_S$g$_S$c$_S$a$_S$c$_S$A$_S$$^m$C$_S$G-3';

(COMP NO 6)
GalNAc-cluster-AM-C6-5'-caA$_S$G$_S$$^m$C$_S$g$_S$a$_S$a$_S$g$_S$t$_S$g$_S$c$_S$a$_S$c$_S$a$_S$C$_S$G$_S$G-3';

(COMP NO 7)
GalNAc-cluster-AM-C6-5'-$^{(5-Br)}$caG$_S$$^m$C$_S$G$_S$t$_S$a$_S$a$_S$a$_S$g$_S$a$_S$g$_S$a$_S$G$_S$G-3';

(COMP NO 8)
GalNAc-cluster-AM-C6-5'-cagcgtaaagagagg-3'; or (COMP NO 9)
GalNAc-cluster-AM-C6$_S$-5'-A$_S$A$_S$T$_S$g$_S$c$_S$t$_S$a$_S$c$_S$a$_S$a$_S$a$_S$c$_S$C$_S$C$_S$A-3', wherein, AM-C6 is a 6-aminohexyl-1-phosphate or 1-thiophosphate linkage;

uppercase letters denote beta-D-oxy-LNA units;

lowercase letters denote DNA units;

s is a phosphorothioate linkage;

m is a DNA or beta-D-oxy-LNA unit containing a 5-methylcytosine base; and

5-Br is a DNA unit containing a 5-bromocytosine base.

18. The method of claim 15, wherein the GalNAc phosphoramidite derivative comprises a GalNAc phosphoramidite derivative of formula Ib

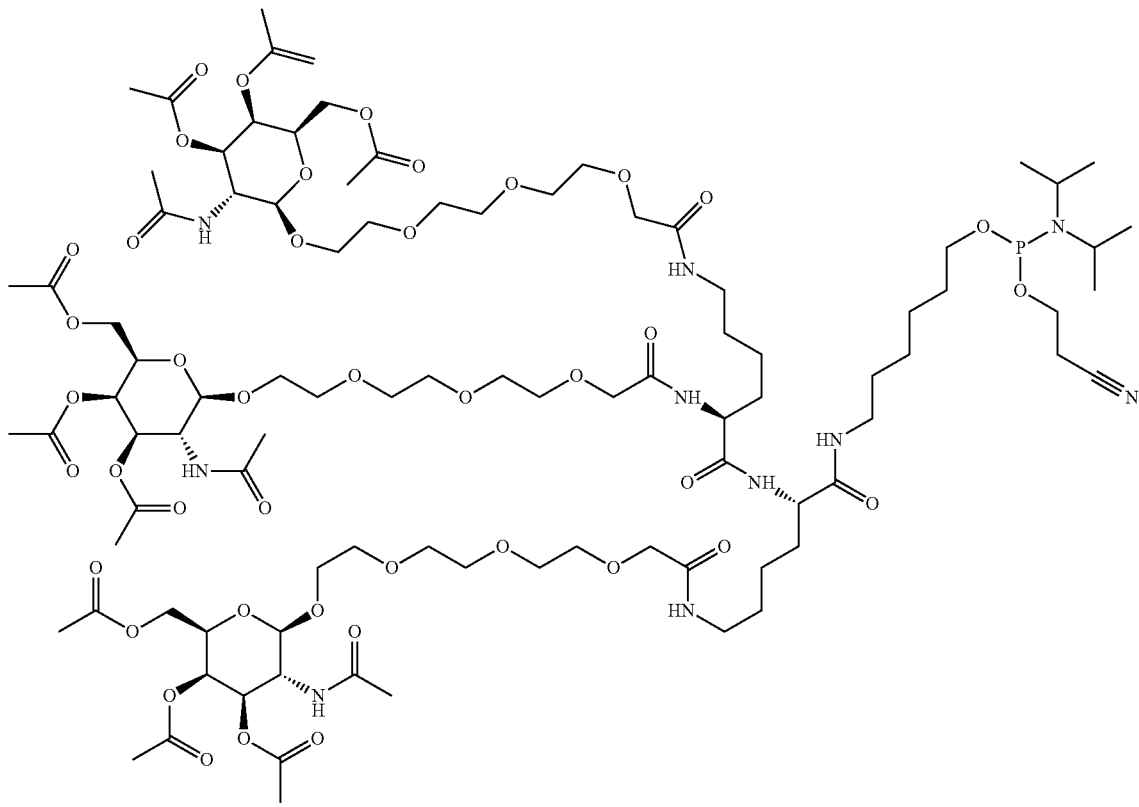

wherein,
R¹ is a hydroxy protecting group;
n is an integer from 0 to 10; and
m is an integer from 0 to 20;
or an enantiomer or optical isomer thereof.

19. The method of claim 15, wherein the GalNAc-cluster oligonucleotide conjugate comprises a nucleobase sequence selected from the group consisting of:

```
                                  (SEQ ID NO: 1)
5'-cagcgtaaagagagg-3';

(SEQ ID NO: 2)
5'-cagcgtaaagagaggt-3';

(SEQ ID NO: 3)
5'-caagcgaagtgcacacg-3';

(SEQ ID NO: 4)
5'-caagcgaagtgcacacgg-3';
and (SEQ ID NO: 5)
5'-aatgctacaaaaccca-3'.
```

* * * * *

SEQUENCE LISTING

```
<160> NUMBER OF SEQ ID NOS: 5

<210> SEQ ID NO 1
<211> LENGTH: 15
<212> TYPE: DNA
<213> ORGANISM: Artificial Sequence
<220> FEATURE:
<223> OTHER INFORMATION: oligonucleotide sequence

<400> SEQUENCE: 1
cagcgtaaag agagg                                                  15

<210> SEQ ID NO 2
<211> LENGTH: 16
<212> TYPE: DNA
<213> ORGANISM: Artificial Sequence
<220> FEATURE:
<223> OTHER INFORMATION: oligonucleotide sequence

<400> SEQUENCE: 2
cagcgtaaag agaggt                                                 16

<210> SEQ ID NO 3
<211> LENGTH: 17
<212> TYPE: DNA
<213> ORGANISM: Artificial Sequence
<220> FEATURE:
<223> OTHER INFORMATION: oligonucleotide sequence

<400> SEQUENCE: 3
caagcgaagt gcacacg                                                17

<210> SEQ ID NO 4
<211> LENGTH: 18
<212> TYPE: DNA
<213> ORGANISM: Artificial Sequence
<220> FEATURE:
<223> OTHER INFORMATION: oligonucleotide sequence
```

```
<400> SEQUENCE: 4
caagcgaagt gcacacgg                                          18

<210> SEQ ID NO 5
<211> LENGTH: 16
<212> TYPE: DNA
<213> ORGANISM: Artificial Sequence
<220> FEATURE:
<223> OTHER INFORMATION: oligonucleotide sequence

<400> SEQUENCE: 5
aatgctacaa aaccca                                            16
```